(12) United States Patent
Upadhya et al.

(10) Patent No.: US 6,221,604 B1
(45) Date of Patent: Apr. 24, 2001

(54) ELECTRON-DEFICIENT NITROGEN HETEROCYCLE-SUBSTITUTED FLUORESCEIN DYES

(75) Inventors: Krishna G. Upadhya, Union City; Steven M. Menchen, Fremont; Weiguo Zhen, Foster City, all of CA (US)

(73) Assignee: PE Corporation, Foster City, CA (US)

( * ) Notice: Subject to any disclaimer, the term of this patent is extended or adjusted under 35 U.S.C. 154(b) by 0 days.

(21) Appl. No.: 09/498,702

(22) Filed: Feb. 7, 2000

(51) Int. Cl.$^7$ .......................... G01N 33/533; C07K 1/13; C07D 405/04
(52) U.S. Cl. ..................... 435/6; 436/546; 436/800; 530/402; 536/24.3; 544/235; 544/238; 544/283; 544/333; 544/353; 544/405; 546/119; 546/144; 546/173; 546/283.1; 548/146; 548/159; 548/215; 548/217; 548/250; 548/256; 548/266.2; 548/305.1; 548/311.4; 548/364.4; 935/8
(58) Field of Search .................... 435/6, 546, 800; 436/546, 800; 530/402; 536/24.32; 544/235, 238, 283, 333, 353, 405; 546/119, 144, 173, 283.1; 548/146, 159, 215, 217, 250, 256, 266.2, 305, 311.4, 364.4; 935/8

(56) References Cited

U.S. PATENT DOCUMENTS

| | | |
|---|---|---|
| 4,318,846 | 3/1982 | Khanna et al. . |
| 5,188,934 | 2/1993 | Menchen et al. . |
| 5,453,505 | 9/1995 | Lee et al. . |
| 5,654,419 | 8/1997 | Mathies et al. . |
| 5,723,591 | 3/1998 | Livak et al. . |
| 5,770,716 | 6/1998 | Khan et al. . |
| 5,800,996 | 9/1998 | Lee et al. . |
| 5,821,356 | 10/1998 | Khan et al. . |
| 5,840,999 | 11/1998 | Benson et al. . |
| 5,863,727 | 1/1999 | Lee et al. . |
| 5,945,526 | 8/1999 | Lee et al. . |
| 6,008,379 | 12/1999 | Benson et al. . |
| 6,020,481 | 2/2000 | Benson et al. . |

FOREIGN PATENT DOCUMENTS

| | | |
|---|---|---|
| 0 251 786 A2 | 1/1988 | (EP) . |
| 0 252 683 A2 | 1/1988 | (EP) . |
| WO 94/05688 | 3/1994 | (WO) . |
| WO 97/36960 | 10/1997 | (WO) . |

OTHER PUBLICATIONS

Acheson, R.M., "Heterocyclic Analogues of Benzene with One Heteroatom," *An Introduction to the Chemistry of Heterocyclic Compounds*, 2$^{nd}$ Ed., pp. 188–199.

Primary Examiner—Mary E. Ceperley
(74) Attorney, Agent, or Firm—Alex Andrus

(57) ABSTRACT

The invention provides compositions electron-deficient nitrogen heterocycle-substituted fluorescein dyes and methods in which the dyes are conjugated to substrates and used as detection labels in molecular biology experiments. The electron-deficient nitrogen heterocycles include pyridine, quinoline, pyrazine, and the like. Substrates include polynucleotides, nucleosides, nucleotides, peptides, proteins, carbohydrates, and ligands.

67 Claims, 14 Drawing Sheets

13

14

15

16

17

18

19

20

21

22

29

30

31

32

33

34

35

36

37    38

39    40

41 pyridazine    pyrimidine    pyrazine    pyridine cinnoline    phthalazine    quinazoline quinoxaline    quinoline    isoquinoline imidazole    pyrazole    1,2,4-triazole    tetrazole benzotriazole    benzotriazine    oxazole    thiazole benzoxazole    benzimidazole    benzothiazole 183                         276
3'FddGTP-EO-13

183                         276
3'FddGTP-EO-6FAM-Bn-dR110

ELECTRON-DEFICIENT NITROGEN HETEROCYCLE-SUBSTITUTED FLUORESCEIN DYES

FIELD OF THE INVENTION

The invention relates generally to the field of fluorescent dye compounds useful as labelling reagents to prepare molecular probes. More specifically, this invention relates to fluorescein dyes with a xanthene ring structure and electron deficient nitrogen heterocycle substituents.

BACKGROUND

The non-radioactive detection of biological analytes utilizing fluorescent labels is an important technology in modern analytical biotechnology. By eliminating the need for radioactive labels, safety is enhanced and the environmental impact and costs associated with reagent disposal are greatly reduced. Examples of methods utilizing such fluorescent detection methods include automated DNA sequencing, oligonucleotide probe methods, detection of polymerase-chain-reaction products, immunoassays, and the like.

In many important applications, it is advantageous to employ multiple spectrally distinguishable fluorescent labels in order to achieve independent detection of a plurality of spatially overlapping analytes, i.e. multiplex fluorescent detection. Examples of methods utilizing multiplex fluorescent detection include single-tube multiplex DNA probe assays, PCR, single nucleotide polymorphisms, immunoassays, and multi-color automated DNA sequencing. The number of reaction vessels may be reduced thereby simplifying experimental protocols and facilitating the production of application-specific reagent kits. In the case of multi-color automated DNA sequencing, multiplex fluorescent detection allows for the analysis of multiple nucleotides in a single electrophoresis lane thereby increasing throughput over single-color methods and reducing uncertainties associated with inter-lane electrophoretic mobility variations. Automated four-color Sanger-type DNA sequencing has enabled entire genome characterization at the molecular level.

Assembling a set of multiple spectrally distinguishable fluorescent labels useful for multiplex fluorescent detection is problematic. Multiplex fluorescent detection imposes at least six severe constraints on the selection of component fluorescent dye labels, particularly for applications requiring a single excitation light source, an electrophoretic separation, and/or treatment with enzymes, e.g., automated DNA sequencing. First, it is difficult to find a set of structurally similar dyes whose emission spectra are spectrally resolved, since the typical emission band half-width for organic fluorescent dyes is about 40–80 nanometers (nm). Second, even if dyes with non-overlapping emission spectra are identified, the set may still not be suitable if the respective fluorescent quantum efficiencies are too low. Third, when several fluorescent dyes are used concurrently, simultaneous excitation becomes difficult because the absorption bands of the dyes are usually widely separated. Fourth, the charge, molecular size, and conformation of the dyes must not adversely affect the electrophoretic mobility of the analyte. Fifth, the fluorescent dyes must be compatible with the chemistry used to create or manipulate the analyte, e.g., DNA synthesis solvents and reagents, buffers, polymerase enzymes, ligase enzymes, and the like. Sixth, the dye must have sufficient photostability to withstand laser excitation.

Currently available multiple dye sets suitable for use in four-color automated DNA sequencing applications require blue or blue-green laser light to adequately excite fluorescence emissions from all of the dyes making up the set, e.g., argon-ion lasers. As lower cost red lasers become available, a need develops for fluorescent dye compounds and their conjugates which satisfy the above constraints and are excitable by laser light having a wavelength above about 500 nm.

SUMMARY

The present invention relates to dye compounds suitable for the creation of sets of spectrally-resolvable fluorescent labels useful for multi-color fluorescent detection.

Generally the dyes of the invention comprise a fluorescein-type, xanthene ring structure I:

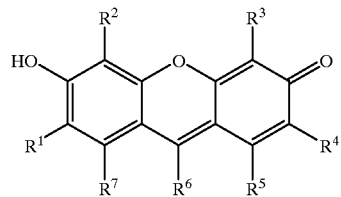

substituted with at least one electron-deficient nitrogen heterocycle linked to the fluorescein ring system at $R^1$, $R^2$, $R^3$, $R^4$, $R^5$, or $R^7$.

$R^1$, when taken alone, is H, F, Cl, $(C_1-C_6)$ alkyl, $(C_1-C_6)$ substituted alkyl, $(C_1-C_6)$ alkoxy, sulfonate, sulfone, amino, imminium, amido, nitrile, reactive linking group, phenyl, substituted phenyl, aryl, substituted aryl, or heterocycle, or when taken together with $R^7$ is benzo or heterocycle.

$R^2$, when taken alone, is H, F, Cl, $(C_1-C_6)$ alkyl, $(C_1-C_6)$ substituted alkyl, $(C_1-C_6)$ alkoxy, sulfonate, sulfone, amino, imminium, amido, nitrile, reactive linking group, phenyl, substituted phenyl, aryl, substituted aryl, or heterocycle.

$R^3$, when taken alone, is H, F, Cl, $(C_1-C_6)$ alkyl, $(C_1-C_6)$ substituted alkyl, $(C_1-C_6)$ alkoxy, sulfonate, sulfone, amino, imminium, amido, nitrile, reactive linking group, phenyl, substituted phenyl, aryl, substituted aryl, or heterocycle.

$R^4$, when taken alone, is H, F, Cl, $(C_1-C_6)$ alkyl, $(C_1-C_6)$ substituted alkyl, $(C_1-C_6)$ alkoxy, sulfonate, sulfone, amino, imminium, amido, nitrile, reactive linking group, phenyl, substituted phenyl, aryl, substituted aryl, or heterocycle, or when taken together with $R^5$ is benzo or heterocycle.

$R^5$, when taken alone, is H, F, Cl, $(C_1-C_6)$ alkyl, $(C_1-C_6)$ substituted alkyl, $(C_1-C_6)$ alkoxy, sulfonate, sulfone, amino, imminium, amido, nitrile, reactive linking group, phenyl, substituted phenyl, aryl, substituted aryl, or heterocycle, or when taken together with $R^4$ is benzo or heterocycle.

$R^7$, when taken alone, is H, F, Cl, $(C_1-C_6)$ alkyl, $(C_1-C_6)$ substituted alkyl, $(C_1-C_6)$ alkoxy, sulfonate, sulfone, amino, imminium, amido, nitrile, reactive linking group, phenyl, substituted phenyl, aryl, substituted aryl, or heterocycle, or when taken together with $R^4$ is benzo or heterocycle.

$R^6$ can be $(C_1-C_6)$ alkyl, $(C_2-C_6)$ alkene, $(C_2-C_6)$ alkyne, cyano, heterocyclic aromatic, phenyl, and substituted phenyl having the structure II:

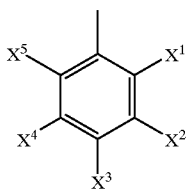

II wherein $X^1$, $X^2$, $X^3$, $X^4$ and $X^5$ taken separately are H, Cl, F, ($C_1$-$C_6$) alkyl, ($C_2$-$C_6$) alkene, ($C_2$-$C_6$) alkyne, $CO_2H$, $SO_3H$, $CH_2OH$, or reactive linking group.

In one aspect, the invention provides a method of labelling a substrate with a fluorescein dye of structure I, where the substrate reacts with the reactive linking group of the dye and a substrate-dye conjugate is formed. Substrate dye-labelled conjugates comprise the electron deficient nitrogen heterocycle-substituted fluorescein dye, according to I, and a substrate, i.e. another molecule or substance. The substrate may be labelled with one or more dyes of the invention, which may be the same or different. Fluorescence from the dyes provides detectable signals across a spectral range, enabling differentiation of differently labelled substrates in a single sample or mixture.

In one embodiment, the electron deficient nitrogen heterocycle-substituted fluorescein dye is covalently conjugated to another dye compound to form an energy-transfer dye compound.

In another embodiment, the electron deficient nitrogen heterocycle-substituted fluorescein dye is covalently conjugated to a nucleoside, nucleotide, nucleoside and nucleotide analog, polynucleotide or polynucleotide analog to form labelled conjugates therewith.

In yet another aspect, the invention provides phosphoramidite reagents including the electron deficient nitrogen heterocycle-substituted fluorescein dyes of the invention.

In another aspect, the invention provides various methods for synthesizing oligonucleotides labelled with electron-deficient nitrogen heterocycle-substituted fluorescein dyes, and employing the dyes for detection of fluorescent labelled polynucleotides.

In another aspect, the invention provides kits comprising electron-deficient nitrogen heterocycle-substituted fluorescein dyes and reagents useful for labelling molecules and/or for performing assays such as DNA sequencing and amplification, e.g. polymerase chain reaction.

The electron-deficient nitrogen heterocycle-substituted fluorescein dyes of the invention provide significant advantages over currently known fluorescein dyes.

DETAILED DESCRIPTION OF THE PREFERRED EMBODIMENTS

Figure 1:
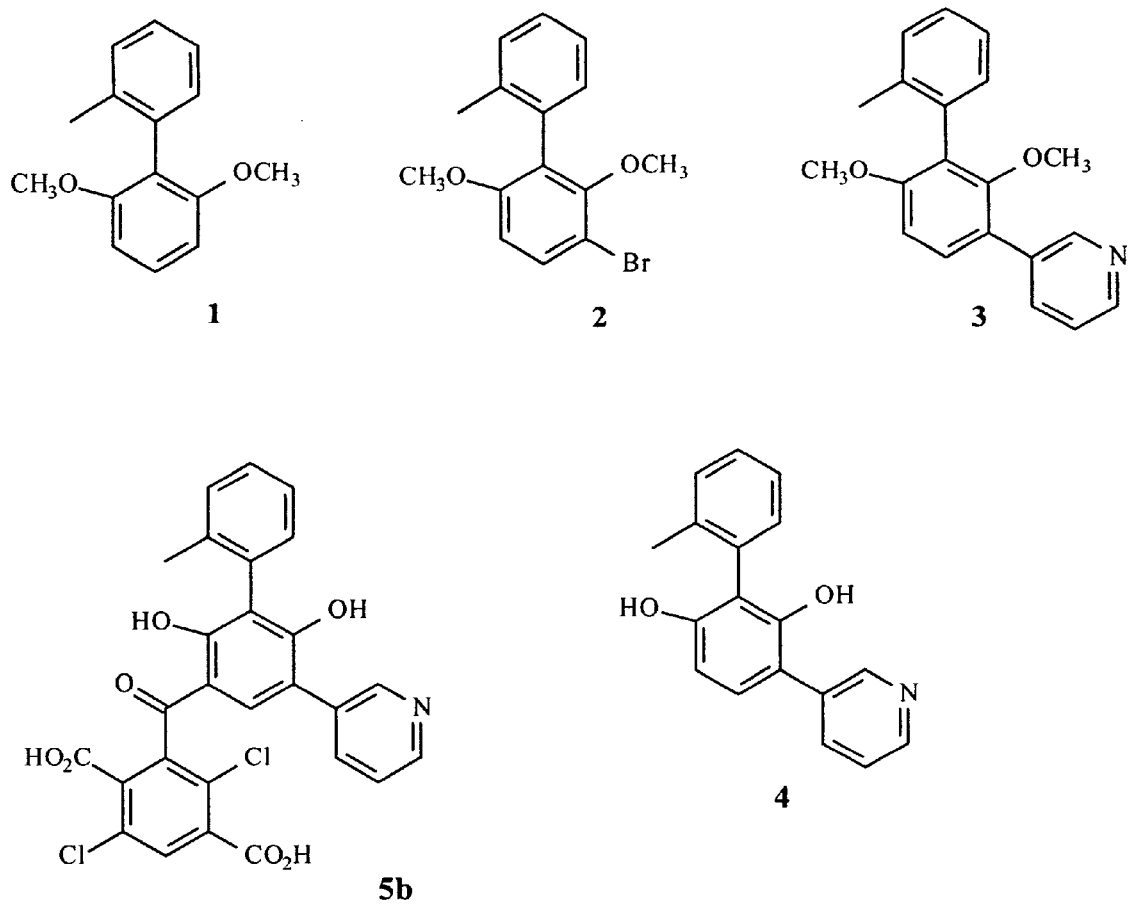
FIG. 1 shows the structures of compounds 1–5

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover all alternatives, modifications, and equivalents, which may be included within the scope of the present invention as defined by the appended claims.

Definitions

Unless stated otherwise, the following terms and phrases as used herein are intended to have the following meanings:

"Nucleobase" means a nitrogen-containing heterocyclic moiety capable of forming Watson-Crick hydrogen bonds with a complementary nucleobase or nucleobase analog, e.g. a purine, a 7-deazapurine, or a pyrimidine. Typical nucleobases are the naturally occurring nucleobases adenine, guanine, cytosine, uracil, thymine, and analogs of the naturally occurring nucleobases, e.g. 7-deazaadenine, 7-deazaguanine, inosine, nebularine, nitropyrrole, nitroindole, 2-amino-purine, 2,6-diamino-purine, hypoxanthine, pseudouridine, pseudocytidine, pseudoisocytidine, 5-propynyl-cytidine, isocytidine, isoguanine, 7-deaza-quanine, 2-thio-pyrimidine, 6-thio-guanine, 4-thio-thymine, 4-thio-uracil, $O^6$-methyl-guanine, $N^6$-methyl-adenine, $O^4$-methyl-thymine, 5,6-dihydrothymine, 5,6-dihydrouracil, 4-methyl-indole, and ethenoadenine (Fasman, *Practical Handbook of Biochemistry and Molecular Biology*, pp. 385–394, CRC Press, Boca Raton, Fla. (1989)).

"Nucleoside" means a compound comprising a nucleobase linked to a C-1' carbon of a ribose sugar. The ribose may be substituted or unsubstituted. Substituted ribose sugars include, but are not limited to, those riboses in which one or more of the carbon atoms, preferably the 3'-carbon atom, is substituted with one or more of the same or different —R, —OR, —NRR or halogen groups, where each R is independently —H, ($C_1$-$C_6$) alkyl or ($C_5$-$C_{14}$) aryl. Particularly preferred riboses are ribose, 2'-deoxyribose, 2',3'-dideoxyribose, 3'-haloribose, 3'-fluororibose, 3'-chlororibose, and 3'-alkylribose. When the nucleobase is A or G, the ribose sugar is attached to the $N^9$-position of the nucleobase. When the nucleobase is C, T or U, the pentose sugar is attached to the $N^1$-position of the nucleobase (Kornberg and Baker, *DNA Replication*, $2^{nd}$ Ed., Freeman, San Francisco, Calif., (1992)).

"Nucleotide" means a phosphate ester of a nucleoside, as a monomer unit or within a polynucleotide. Nucleotides are sometimes denoted as "NTP", or "dNTP" and "ddNTP" to particularly point out the structural features of the ribose sugar. "Nucleotide 5'-triphosphate" refers to a nucleotide with a triphosphate ester group at the 5' position. The triphosphate ester group may include sulfur substitutions for the various oxygens, e.g. α-thio-nucleotide 5'-triphosphates.

As used herein, the terms "polynucleotide" or "oligonucleotide" encompass any polymer compound comprised of nucleosides, nucleotides or analogs thereof. "Oligonucleotide" and "polynucleotide", used interchangeably, mean single-stranded and double-stranded polymers of nucleotide monomers, including 2'-deoxyribonucleotides (DNA) and ribonucleotides (RNA). An oligonucleotide may be composed entirely of deoxyribonucleotides, entirely of ribonucleotides, or chimeric mixtures thereof, linked by internucleotide phosphodiester bond linkages, or internucleotide analogs, and associated counterions, e.g., $H^+$, $N_4^+$, trialkylammonium, $Mg^{2+}$, $Na^+$ and the like. Oligonucleotides may be comprised of nucleobase and sugar analogs. Polynucleotides typically range in size from a few monomeric units, e.g. 5–40 when they are commonly referred to as oligonucleotides, to several thousands of monomeric nucleotide units. Unless denoted otherwise, whenever an oligonucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted.

The term "Watson/Crick base-pairing" refers to the hydrogen-bonding base pairing commonly observed in double-stranded DNA.

"Attachment site" refers to a site on a moiety, e.g. a fluorescein dye, a nucleotide, or an oligonucleotide, to which a linker is covalently attached.

"Linker" refers to a moiety that links a dye to a substrate, e.g. an oligonucleotide, or one dye to another, e.g. in an energy-transfer dye pair.

"Alkyl" refers to a saturated or unsaturated, straight-chain, branched, or cyclic hydrocarbon radical derived by the removal of one hydrogen atom from a single carbon atom of a parent alkane, alkene, or alkyne. Typical alkyl groups include, but are not limited to, methyl, ethyl, propyl, butyl, and the like. Typical alkyl groups include, but are not limited to, methyl (—$CH_3$); ethyls such as ethanyl (—$CH_2$—$CH_3$), ethenyl (—CH=$CH_2$), ethynyl (—C≡CH); propyls such as propan-1-yl (—$CH_2$—$CH_2$—$CH_3$), propan-2-yl, cyclopropan-1-yl, prop-1-en-1-yl (—CH=CH—$CH_2$), prop-1-en-2-yl, prop-2-en-1-yl (—$CH_2$—CH=$CH_2$), prop-2-en-2-yl, cycloprop-1-en-1-yl; cycloprop-2-en-1-yl, prop-1-yn-1-yl (—C≡C—$CH_3$), prop-2-yn-1-yl (—$CH_2$—C≡CH), etc.; butyls such as butan-1-yl (—$CH_2$—$CH_2$—$CH_2$—$CH_3$), butan-2-yl, cyclobutan-1-yl, but-1-en-1-yl (—CH=$CH_2$—$CH_2$—$CH_3$), but-1-en-2-yl, but-2-en-1-yl (—$CH_2$—CH=$CH_2$—$CH_3$), but-2-en-2-yl, buta-1,3-dien-1-yl (—CH=CH—CH=$CH_2$), buta-1,3-dien-2-yl, cyclobut-1-en-1-yl, cyclobut-1-en-3-yl, cyclobuta-1,3-dien-1-yl, but-1-yn-1-yl (—C≡C—$CH_2$—$CH_3$), but-1-yn-3-yl, but-3-yn-1-yl (—$CH_2$—$CH_2$—C≡CH), etc.; and the like. In preferred embodiments, the alkyl groups are ($C_1$–$C_6$) alkyl, with ($C_1$–$C_3$) being particularly preferred.

"Alkoxy" means —OR where R is ($C_1$–$C_6$) alkyl.

"Alkyldiyl" refers to a saturated or unsaturated, branched, straight chain or cyclic hydrocarbon radical of 1–12 carbon atoms and having two monovalent radical centers derived by the removal of two hydrogen atoms from the same or two different carbon atoms of a parent alkane, alkene or alkyne. Typical alkyldiyl radicals include, but are not limited to, methano (—$CH_2$—); 1,2-ethyldiyl; 1,3-propyldiyl; 1,4-butyldiyl; and the like.

"Aryl" refers to a monovalent aromatic hydrocarbon radical of 6–20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Aryldiyl" refers to an unsaturated cyclic or polycyclic hydrocarbon radical of 6–20 carbon atoms having a conjugated resonance electron system and at least two monovalent radical centers derived by the removal of two hydrogen atoms from two different carbon atoms of a parent aryl compound.

"Substituted alkyl", "substituted alkyldiyl", "substituted aryl" and "substituted aryldiyl" refer to alkyl, alkyldiyl radicals, aryl and aryldiyl respectively, in which one or more hydrogen atoms are each independently replaced with another substituent. Typical substituents include, but are not limited to, —X, —R, —$O^-$, —OR, —SR, —$S^-$, —NRR, =NR, —$CX_3$, —CN, —OCN, —SCN, —NCO, —NCS, —NO, —$NO_2$, =$N_2$, —$N_3$, —$S(O)_2O^-$, —$S(O)_2OH$, —$S(O)_2R$, —$P(O)(O^-)_2$, —$P(O)(OH)_2$, —C(O)R, —C(O)X, —C(S)R, —C(O)OR, —C(O)$O^-$, —C(S)OR, —C(O)SR, —C(S)SR, —C(O)NRR, —C(S)NRR and —C(NR)NRR, where each X is independently a halogen and each R is independently —H, alkyl, aryl, or heterocycle. Particularly preferred substituents are halogen, —$OS(O)_2OR$, —$S(O)_2OR$, —$S(O)_2R$, —$S(O)_2NR$, —S(O)R, —$OP(O)O_2RR$, —$P(O)O_2RR$, —C(O)OR, —NRR, —NRRR, —NC(O)R, —C(O)R, —C(O)NRR, —CN, —O and —OR, wherein R is independently selected from the group consisting of —H, alkyl, aryl, heteroaryl, heterocycle and linking group.

"Reactive linking group" refers to a chemically reactive moiety, e.g. a nucleophile or electrophile, capable of reacting with another molecule to form a covalent bond, or linkage.

"Heterocycle" refers to a molecule with a ring system in which one or more ring atoms have been replaced with a heteroatom, e.g. nitrogen, oxygen, and sulfur.

"Electron-deficient nitrogen heterocycle substituent" refers to a monovalent electron-deficient nitrogen heterocycle derived by the removal of one hydrogen atom from a single atom of the ring system to join the heterocycle to the fluorescein dyes of the invention (Joule, etal, *Heterocyclic Chemistry*, 3rd Ed., Stanley Thornes Publisher, Ltd., Cheltenham, U.K. (1998); Acheson, R., *An Introduction to the Chemistry of Heterocyclic Compounds*, 2nd Ed. Interscience Publishers, division of John Wiley & Sons, New York (1967)). Several examplary electron-deficient nitrogen heterocycles are set forth in FIG. 11.

"Substrate" is an entity to which dye compounds of the present invention are attached. Substrates include, but are not limited to a (i) polynucleotide, (ii) nucleoside and nucleotide, (iii) peptide and protein, (iv) carbohydrate, (v) ligand, and (vi) any analog of the preceding (i) to (v).

"Enzymatically incorporatable" refers to a property of a nucleotide in which it is capable of being enzymatically incorporated onto the terminus, e.g. 3', of a nascent polynucleotide chain through the action of a polymerase enzyme.

"Terminator" means an enzymatically incorporatable nucleotide which prevents subsequent incorporations of nucleotides to the resulting polynucleotide chain and thereby halt polymerase extension. Typical terminators lack a 3'-hydroxyl substituent and include 2',3'-dideoxyribose, 2',3'-didehydroribose, and 2',3'-dideoxy, 3'-haloribose, e.g. 3'-fluoro. Alternatively, a ribofuranose analog could be used, such as arabinose. Exemplary nucleotide terminators include 2',3'-dideoxy-β-D-ribofuranosyl, β-D-arabinofuranosyl, 3'-deoxy-β-D-arabinofuranosyl, 3'-amino-2',3'-dideoxy-β-D-ribofuranosyl, and 2',3'-dideoxy-3'-fluoro-β-D-ribofuranosyl (Chidgeavadze etal. (1984) Nucleic Acids Res., 12: 1671–1686; and Chidgeavadze etal. (1985) FEB. Lett., 183: 275–278). Nucleotide terminators also include reversible nucleotide terminators (Metzker etal. (1994) Nucleic Acids Res., 22(20): 4259).

"Enzymatically extendable" means a property of a nucleotide in which it is enzymatically incorporatable at the terminus of a polynucleotide and the resulting extended polynucleotide can undergo subsequent incorporations of nucleotides or nucleotide analogs.

"Internucleotide analog" means a phosphate ester analog of oligonucleotides which include, but are not limited to, alkylphosphonates, methylphosphonates, phosphoramidates, phosphotriesters, phosphorothioates, phosphorodithioates, phosphoroamidates. Internucleotide analogs also include non-phosphate analogs where the sugar/phosphate group is replaced by amide linkages, such as 2-aminoethylglycine units, referred to as PNA (Nielsen, etal, (1991) "Sequence-selective recognition of DNA by strand displacement with a thymidine-substituted polyamide", Science 254:1497–1500).

"Target sequence" means a polynucleotide, DNA or RNA, single-stranded or double-stranded that is the subject of hybridization with a primer or probe, enzymatic activity, or detection.

"Spectrally Resolvable" means, in reference to a set of fluorescent dyes, that the fluorescence emission bands of the respective dyes are sufficiently distinct, i.e., sufficiently non-overlapping, that the dyes, either alone or when conjugated to other compounds (labelled), are distinguishable from one another on the basis of their fluorescence signals using standard photodetection systems such as photodetectors employing a series of band pass filters and photomultiplier tubes, charged-coupled devices (CCD), spectrographs, etc. (Wheeless et al., (1985) *Flow Cytometry: Instrumentation and Data Analysis*, pp. 21–76, Academic Press, New York). Preferably, all of the dyes comprising a spectrally resolvable set of dyes are excitable by a single light source.

"Mobility-Matched" refers to a set of fluorescent dyes that, when used to label polynucleotides of equal lengths, yields differentially labelled polynucleotides having substantially similar electrophoretic mobilities. Typically, the relative electrophoretic mobilities of polynucleotides labelled with a set of mobility-matched dyes will vary by less than about one-half nucleotide. Preferably, the mobility-matched dyes are spectrally resolvable, as previously defined.

"Relative photostability" means the chemical stability of fluorescent dyes relative to a standard reference, 5-carboxyfluorescein, as measured by exposure to high-intensity white light with sampling measurement of remaining dye at its absorption maxima. Equal optical density units of the test dye and the reference are subjected in parallel to light, as a correlative test for stability under the laser-induced fluorescence common to automated DNA sequencing and fragment analysis applications.

Dyes

In a first aspect, the present invention comprises a novel class of fluorescein-type, xanthene ring compounds, according to structure I:

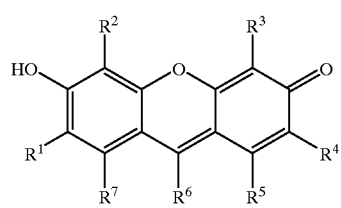

I substituted with at least one electron-deficient nitrogen heterocycle linked to the fluorescein ring system at $R^1$, $R^2$, $R^3$, $R^4$, $R^5$, or $R^7$. The electron-deficient nitrogen heterocycle may be linked to the fluorescein ring system through a carbon-carbon bond or a carbon-nitrogen bond. All molecular structures provided throughout this disclosure are intended to encompass not only the exact electronic structure presented, but also include all resonant structures, tautomers, enantiomers, diastereomers, and protonation states thereof $R^1$, when taken alone, is H, F, Cl, ($C_1$–$C_6$) alkyl, ($C_1$–$C_6$) substituted alkyl, ($C_1$–$C_6$) alkoxy, sulfonate, sulfone, amino, imminium, amido, nitrile, reactive linking group, phenyl, substituted phenyl, aryl, substituted aryl, or heterocycle, or when taken together with $R^7$ is benzo or heterocycle.

$R^2$, when taken alone, is H, F, Cl, ($C_1$–$C_6$) alkyl, ($C_1$–$C_6$) substituted alkyl, ($C_1$–$C_6$) alkoxy, sulfonate, sulfone, amino, imminium, amido, nitrile, reactive linking group, phenyl, substituted phenyl, aryl, substituted aryl, or heterocycle.

$R^3$, when taken alone, is H, F, Cl, ($C_1$–$C_6$) alkyl, ($C_1$–$C_6$) substituted alkyl, ($C_1$–$C_6$) alkoxy, sulfonate, sulfone, amino, imminium, amido, nitrile, reactive linking group, phenyl, substituted phenyl, aryl, substituted aryl, or heterocycle.

$R^4$, when taken alone, is H, F, Cl, ($C_1$–$C_6$) alkyl, ($C_1$–$C_6$) substituted alkyl, ($C_1$–$C_6$) alkoxy, sulfonate, sulfone, amino, imminium, amido, nitrile, reactive linking group, phenyl, substituted phenyl, aryl, substituted aryl, or heterocycle, or when taken together with $R^5$ is benzo or heterocycle.

$R^5$, when taken alone, is H, F, Cl, ($C_1$–$C_6$) alkyl, ($C_1$–$C_6$) substituted alkyl, ($C_1$–$C_6$) alkoxy, sulfonate, sulfone, amino, imminium, amido, nitrile, reactive linking group, phenyl, substituted phenyl, aryl, substituted aryl, or heterocycle, or when taken together with $R^4$ is benzo or heterocycle.

$R^7$, when taken alone, is H, F, Cl, ($C_1$–$C_6$) alkyl, ($C_1$–$C_6$) substituted alkyl, ($C_1$–$C_6$) alkoxy, sulfonate, sulfone, amino, imminium, amido, nitrile, reactive linking group, phenyl, substituted phenyl, aryl, substituted aryl, or heterocycle, or when taken together with R' is benzo or heterocycle.

$R^6$ is selected from the group consisting of ($C_1$$C_6$) alkyl, ($C_2$–$C_6$) alkene, ($C_2$–$C_6$) alkyne, cyano, heterocyclic aromatic, phenyl, and substituted phenyl having the structure II:

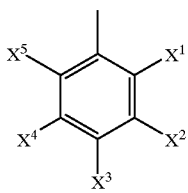

II wherein $X^1$, $X^2$, $X^3$, $X^4$ and $X^5$ taken separately are H, Cl, F, ($C_1$–$C_6$) alkyl, ($C_2$–$C_6$) alkene, ($C_2$–$C_6$) alkyne, $CO_2H$, $SO_3H$, $CH_2OH$, or reactive linking group.

Particularly preferred dyes according to I include where $R^4$ taken together with $R^5$ forms a fused ring, e.g. benzo. Likewise preferred is where $R^1$ taken together with $R^7$ forms a fused ring, e.g. benzo.

Preferred dyes include where $R^1$, $R^2$, $R^3$ and $R^4$, each taken separately, are phenyl and substituted phenyl, naphthyl, substituted naphthyl, fluoro, chloro, 2-pyridyl, 3-pyridyl, 2-quinolyl or 3-quinolyl. $R^5$ and $R^7$ are preferably hydrogen.

Another class of particularly preferred dyes according to II includes those where the substituted phenyl has structure IIa:

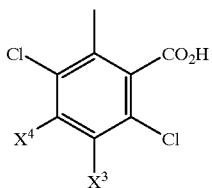

IIa

A preferred embodiment of IIa is where one of $X^3$ and $X^4$ is a reactive linking group and the other is hydrogen. A particularly preferred embodiment of IIa is where one of $X^3$ and $X^4$ is carboxyl and the other is hydrogen.

Various aspects of the above-described invention enable one or more of the following important advantages over known fluorescent dye compounds useful for multiplex fluorescent detection: (1) the emission spectra of the subject dye compounds can be modulated by minor variations in the type and location of the electron-deficient nitrogen heterocycle and/or aryl-substituents, allowing for the creation of dye sets having similar absorption characteristics yet spectrally resolvable fluorescence emission spectra; (2) the subject dye compounds may be easily attached to substrates without compromising their favorable fluorescence properties; (3) the subject dye compounds have narrow emission bandwidths, i.e., the emission bandwidth has a full-width at half the maximum (FWHM) emission intensity of below about 45 nm; (4) the subject dye compounds are highly soluble in buffered aqueous solution while retaining a high quantum yield; (5) the subject dye compounds are relatively photostable; and (6) the subject dye compounds have relatively large extinction coefficients, i.e., greater than about 50,000 (Benson etal "Aromatic-substituted xanthene dyes", U.S. Pat. No. 6,008,379, issued Dec. 28, 1999). Narrow emission bandwidths, as exemplified by FWHM, are desirable as facilitating spectral resolution in a mixture of substrates labelled with more than one (a set) fluorescent dye. Photostability is an important property in that substrates, e.g. polynucleotides, labelled with the dyes of the invention may be subjected to intense laser light to induce fluorescence for detection. Photobleaching, or other chemical degradation mechanisms, diminish or prevent detection of substrates labelled with dyes of less than optimal photostability.

Figure 11:
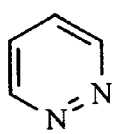
FIG. 11 shows a representative collection of electron-deficient nitrogen heterocycles
Figure 11:
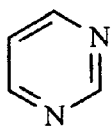
Figure 11:
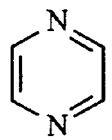
Figure 11:
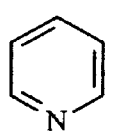
Figure 11:
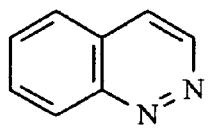
Figure 11:
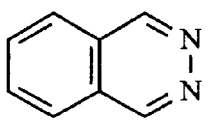
Figure 11:
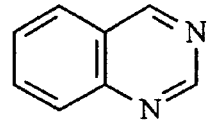
Figure 11:
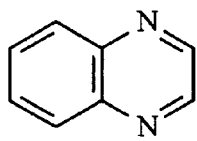
Figure 11:
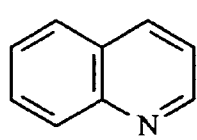
Figure 11:
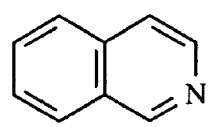
Figure 11:
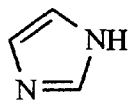
Figure 11:
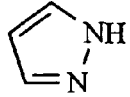
Figure 11:
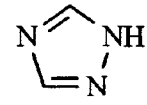
Figure 11:
Figure 11:
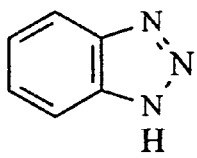
Figure 11:
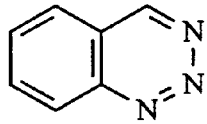
Figure 11:
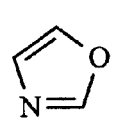
Figure 11:
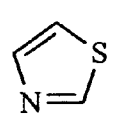
Figure 11:
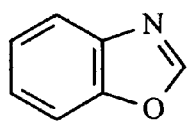
Figure 11:
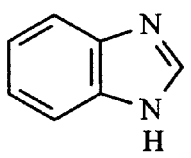
Figure 11:
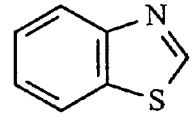
Figure 12:
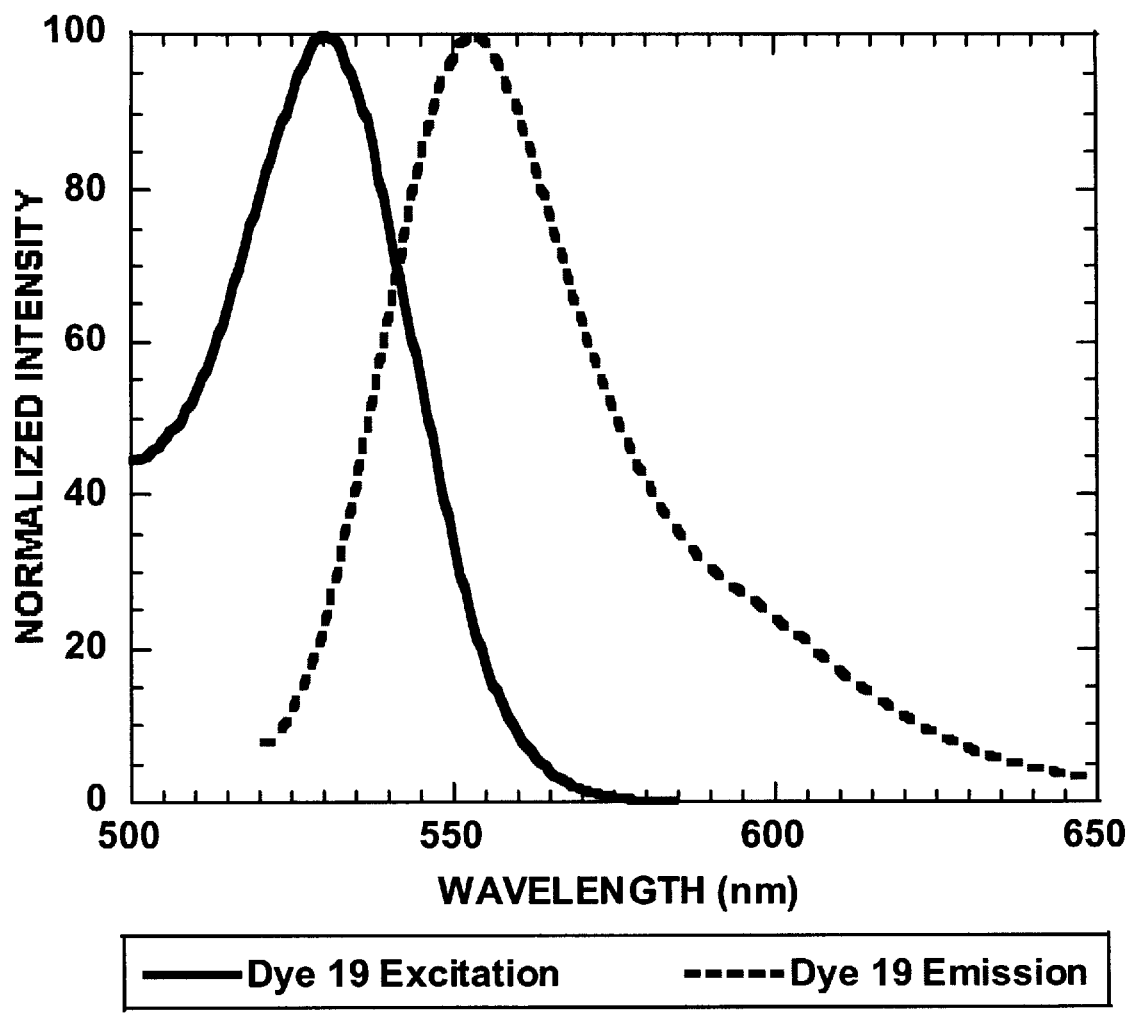
FIG. 12 shows fluorimetry scans of compound 19; Excitation max. 530 nm, Emission max. 554 nm. in 1×TBE at room temperature
Figure 13:
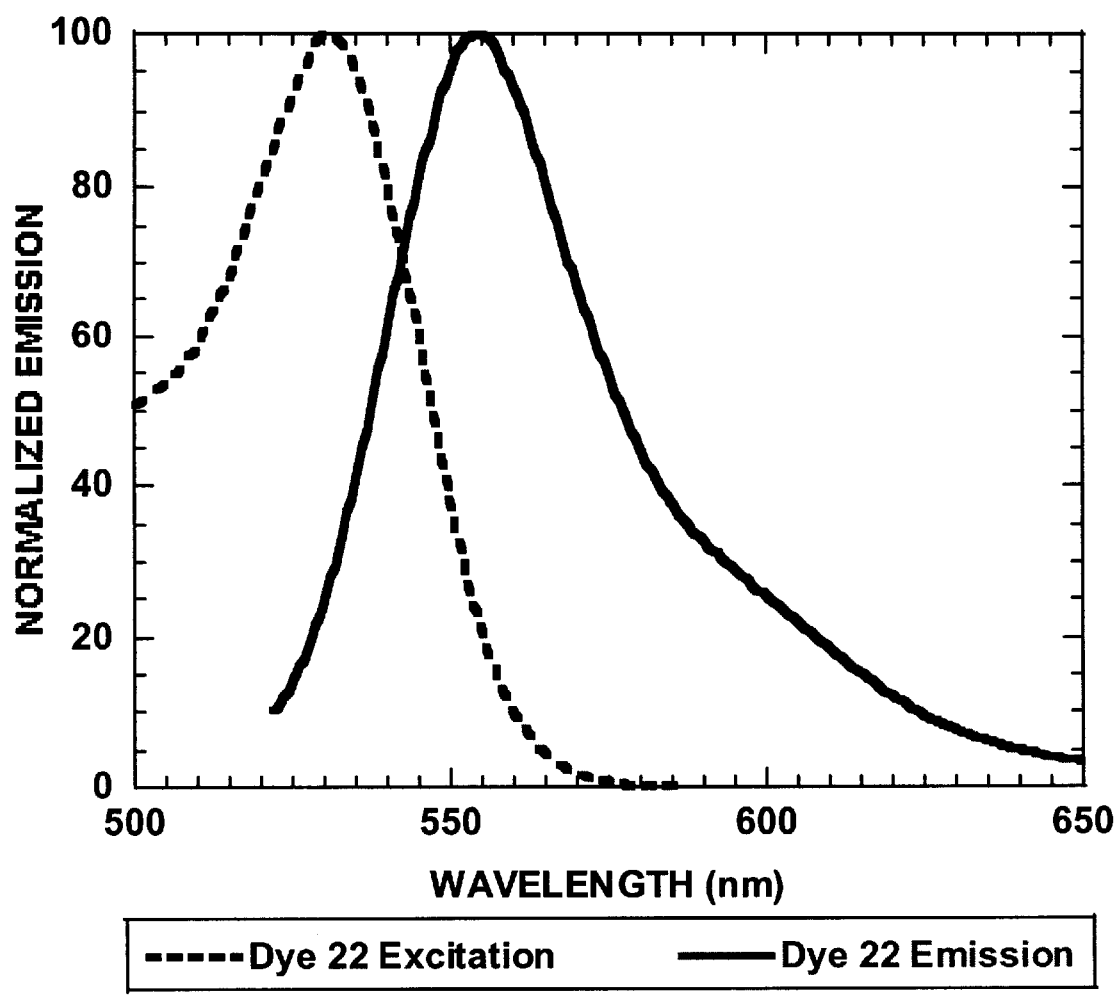
FIG. 13 shows fluorimetry scans of compound 22; Excitation max. 531.5 nm, Emission max. 556 nm. in 1×TBE at room temperature
Figure 14:
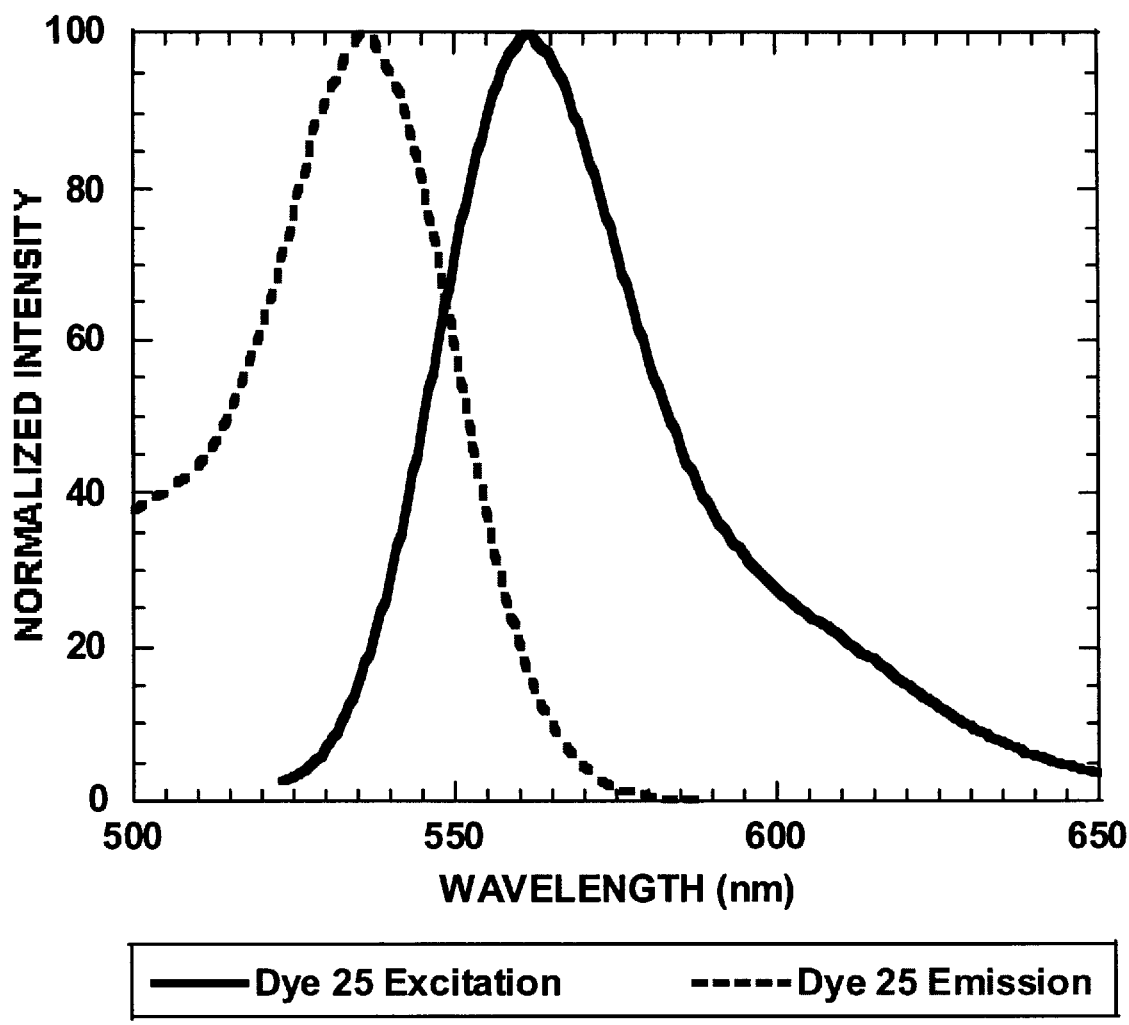
FIG. 14 shows a fluorimetry scan of compound 25; Emission max. 562.5 nm. in 1×TBE at room temperature
Figure 15:
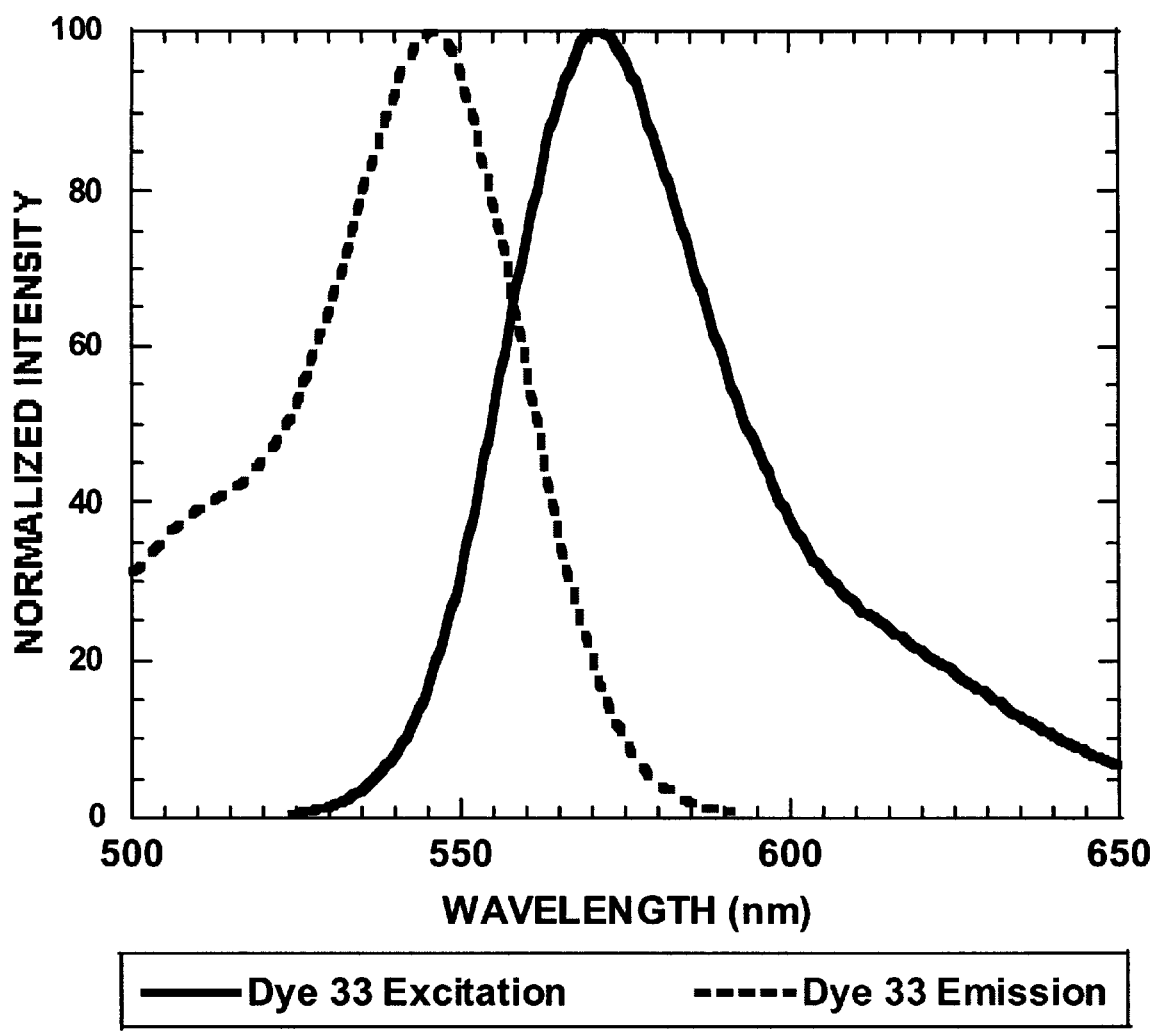
FIG. 15 shows fluorimetry scans of compound 33; Excitation max. 545.5 nm, Emission max. 571.5 nm. in 1×TBE at room temperature

FIG. 11 shows a representative sample of electron-deficient nitrogen heterocycles which may be used as substituents on the fluorescein dyes of the invention. These heterocycle substituents have direct effects on important spectral properties of fluorescent dyes. These effects are exemplified by the spectral properties of fluorescein dyes of the present invention such as: (i) excitation, emission, and-absorption maxima and spectra, (ii) photostability, (iii) quantum efficiency, and (iv) energy-transfer efficiency.

Electron-deficient nitrogen heterocycles may have one 5- or 6-membered ring bearing one or more nitrogen atoms in the ring (FIG. 11). The 5- or 6-membered ring may be fused to a second aromatic ring, e.g. a benzo or substituted-benzo ring, or saturated ring, e.g. cyclopentyl or cyclohexyl. The heterocycle may bear other heteroatoms, e.g. oxygen or sulfur, in the ring system.

Figure 2:
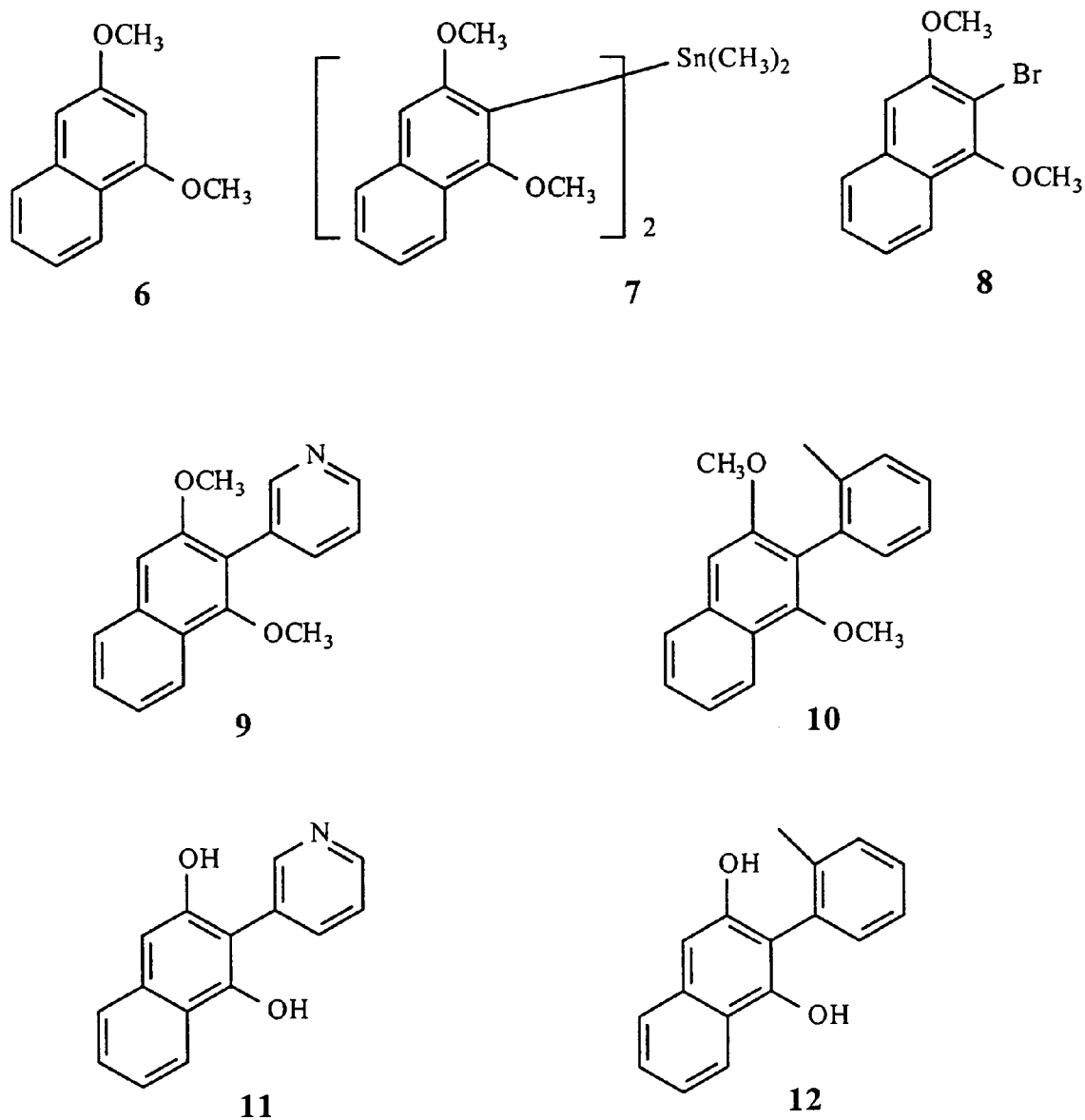
FIG. 2 shows the structures of compounds 6–12

Preferred electron-deficient nitrogen heterocycles include, but are not limited to those in FIG. 11 and 2-pyridyl, 3-pyridyl, 4-pyridyl, 2-quinolyl, 3-quinolyl, 4-quinolyl, 2-imidazole, 4-imidazole, 3-pyrazole, 4-pyrazole, pyridazine, pyrimidine, pyrazine, cinnoline, pthalazine, quinazoline, quinoxaline, 3-(1,2,4-N)-triazolyl, 5-(1,2,4-N)-triazolyl, 5-tetrazolyl, 4-(1-O, 3N)-oxazole, 5-(1-O, 3-N)-oxazole, 4-(1-S, 3-N)-thiazole, 5-(1-S, 3-N)-thiazole, 2-benzoxazole, 2benzothiazole, benzotriazole, 4-(1,2,3-N)-benzotriazine, and benzimidazole. The heterocycle may be attached to the xanthene ring system directly by a bond with a carbon atom of the heterocycle ring. Alternatively, the heterocycle may be attached to the xanthene ring system through an unsaturated linker which extends delocalization of aromaticity between the heterocycle and the xanthene ring system. Linkers that permit extensive electronic delocalization include, but are not limited to: (i) olefinic; —CR═CR—, (ii) polyolefinic; —(CR═CR)$_n$— where n is 2 to 10, (iii) acetylenic; —C≡C—, (iv) polyacetylenic; —(C≡C)$_n$— where n is 2 to 10, (v) squarine, and (vi) other cyclic conjugated linkers. R is selected from the group consisting of hydrogen, ($C_1$–$C_6$) alkyl, halogen, fluorine, chlorine, CN, $CF_3$, aryl, and substituted aryl. The geometry of the olefinic linkages may be cis or trans, E or Z.

Energy Transfer Dyes

In another aspect, the present invention comprises energy transfer dye compounds incorporating the electron-deficient nitrogen heterocycle-substituted fluorescein dye compounds of structure I. Generally, the energy transfer dyes of the present invention include a donor dye which absorbs light at a first wavelength and emits excitation energy in response, an acceptor dye which is capable of absorbing the excitation energy emitted by the donor dye and fluorescing at a second wavelength in response, and a linker which attaches the donor dye to the acceptor dye, the linker being effective to facilitate efficient energy transfer between the donor and acceptor dyes and to maintain a high emission quantum yield of the acceptor dye (Lee, etal "Energy transfer dyes with enhanced fluorescence", U.S. Pat. No. 5,800,996, issued Sep. 1, 1998; Lee, etal "Energy transfer dyes with enhanced fluorescence", U.S. Pat. No. 5,945,526, issued Aug. 31, 1999; Mathies, etal "Fluorescent labels and their use in separations", U.S. Pat. No. 5,654,419, issued Aug. 5, 1997). In the energy transfer dye of the invention, at least one of the donor acceptor dyes is an electron-deficient nitrogen heterocycle-substituted fluorescein dye.

Energy transfer dyes have advantages for use in the simultaneous detection of multiple labelled substrates in a mixture, such as DNA sequencing. A single donor dye can be used in a set of energy transfer dyes so that each dye pair has strong absorption at a common wavelength. By then varying the acceptor dye in the energy transfer set, the acceptor dyes can be spectrally resolved by their respective emission maxima. Energy transfer dyes also provide a larger effective Stokes shift than non-energy transfer dyes. The Stokes shift is the difference between the excitation maximum, the wavelength at which the donor dye maximally absorbs light, and the emission maximum, the wavelength at which the acceptor maximally emits light.

In a preferred embodiment, the linker between the donor dye and acceptor dye includes a functional group which gives the linker some degree of structural rigidity, such as an alkene, diene, an alkyne, a five and six membered ring having at least one unsaturated bond or a fused ring structure. The donor dye and the acceptor dye of the energy transfer dye may be attached by linkers which have the structures:

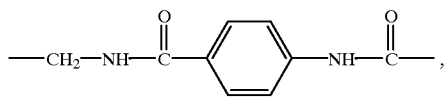

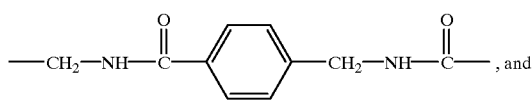

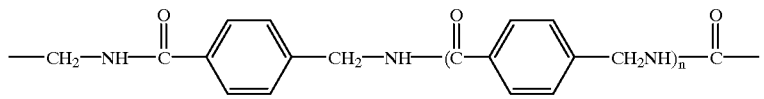

wherein n is 1 or 2.

The attachment sites of the linker between the donor dye and acceptor dye of an energy transfer dye may be at any position $R^1$–$R^7$ where one or both of the donor dye and acceptor dye is a dye of the present invention. Preferred attachment sites include $R^2$, $R^3$, $X^3$, and $X^4$.

The energy transfer dye compound is covalently attached to a substrate through a linker. The linker may be alkyldiyl ($C_1$–$C_{12}$) or aryldiyl ($C_6$–$C_{20}$) and bearing functional groups including amide, carbamate, urea, thiourea, phosphate, phosphorothioate, and the like. Preferred linkers include 1,2-ethyldiyl and 1,6-hexyldiyl. The attachment sites of the linker between the energy transfer dye and the substrate may be at any position $R^1$–$R^7$ on the energy transfer dye, where one or both of the donor dye and acceptor dye is a dye of the present invention. Preferred attachment sites include $R^2$, $R^3$, $X^3$, and $X^4$. Where the substrate is a nucleoside or nucleotide, a preferred attachment site is on the nucleobase. Where the substrate is an oligonucleotide, preferred attachment sites include the 3' and 5' terminii. Where the substrate is a peptide or protein, preferred attachment sites include the amino and carboxyl terminii.

Methods of Synthesis

Several synthetic methods are available for the synthesis of the fluorescein dyes of the invention. A preferred method of synthesis of intermediates is via the palladium-catalyzed Suzuki boronate coupling reaction whereby an aryl boronic acid is coupled with an aryl halide to give a biaryl product with regioselectivity (Zhang, etal (1998) "Base and cation effects on the Suzuki cross-coupling of bulky arylboronic acid with halopyridines: synthesis of pyridylphenols", J. Org. Chem. 63:6886–90; Martin, etal (1993) "Palladium-catalyzed cross-coupling reactions of organoboronic acids with organic electrophiles", Acta Chemica Scan. 47:221–30; Aliprantis, etal (1994) "Observation of catalytic intermediates in the Suzuki reaction by electrospray mass spectrometry", J. Am. Chem. Soc. 116:6985–86; Thompson, etal (1984) "A general synthesis of 5-arylnicotinates", J. Org. Chem. 49:5237–43).

Cyclization substrate 5 is synthesized in FIG. 1. The Suzuki reaction is iterated, first by coupling 1,3-dimethoxyphen-2-yl boronic acid with 2-bromotoluene with tetrakis(triphenylphosphine) palladium catalysis to give biphenyl compound 1. Regioselective bromination of 1 gave 2, followed by Suzuki reaction with pyridine-3-boronic acid under palladium catalysis to yield 3. Demethylation of 3 with hydrobromic acid and acetic acid gave 4, followed by Friedel-Crafts acylation with 2,5-dichlorotrimellitic anhydride to yield 5.

Brominated naphthyl compound 8 serves as a common intermediate for the synthesis of cyclization intermediates 11 and 12, illustrated in FIG. 2. Suzuki coupling of pyridine-3-boronic acid and tol-2-yl boronic acid gave 9 and 10, respectively, which were demethylated to 11 and 12.

Figure 3:
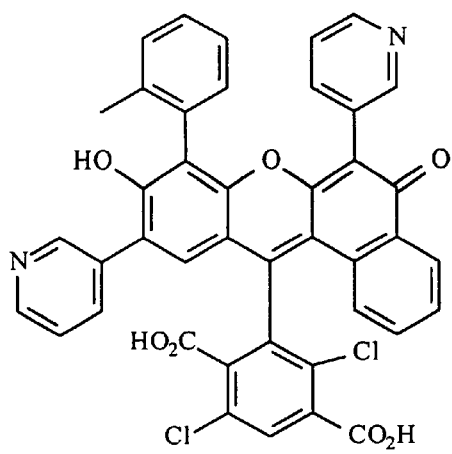
FIG. 3 shows the structures of compounds 13 and 14
Figure 3:
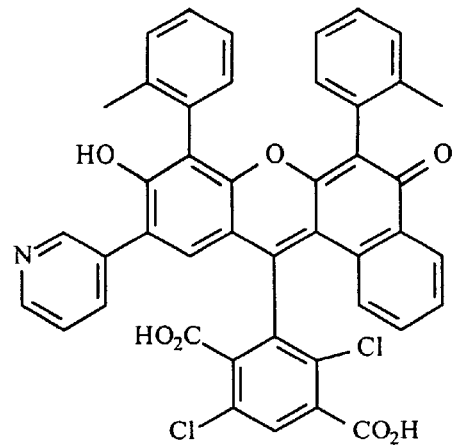
Figure 4:
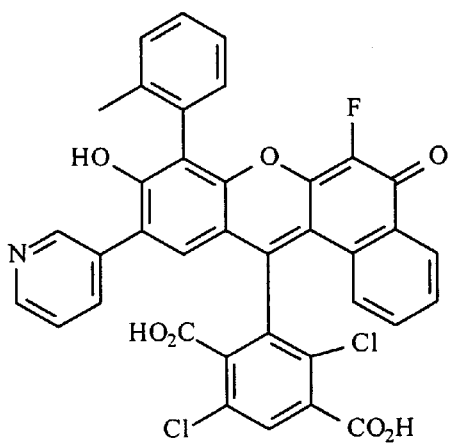
FIG. 4 shows the structures of compounds 15 and 16
Figure 4:
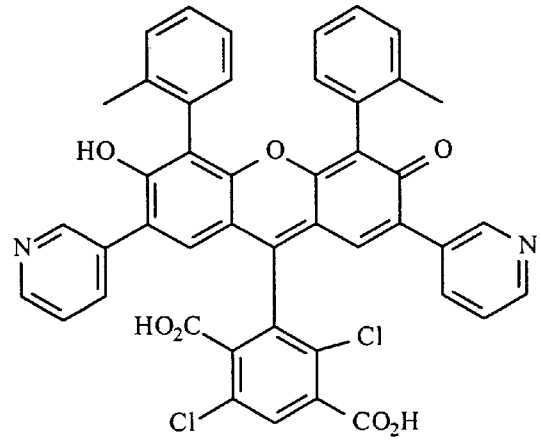

Cyclization of an equimolar mixture of intermediates 5 and 11 in methanesulfonic acid at 100° C. gave 30% yield of dye Z13 (FIG. 3) after chromatography (Example 13). Likewise, 14 was formed by cyclization of 5 with 12 (Example 14). Dye 15 (FIG. 4) was formed by cyclization of 5 and 2-fluoro-1,3-dihydroxynaphthalene (Benson, etal "Asymmetric benzoxanthene dyes", U.S. Pat. No. 5,840, 999, issued Nov. 24, 1998). Symmetric dye 16 (FIG. 4) was synthesized by double cyclization of two molar equivalents of 4 and one molar equivalent 2,5-dichlorotrimellitic anhydride (Example 16).

Figure 5:
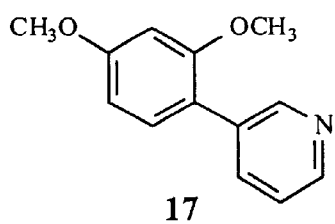
FIG. 5 shows the structures of compounds 17–22
Figure 5:
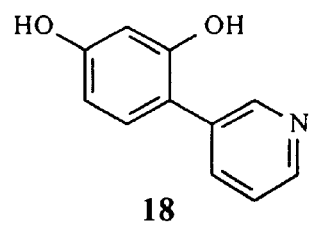
Figure 5:
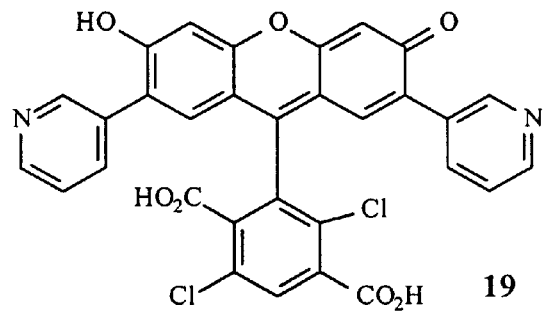
Figure 5:
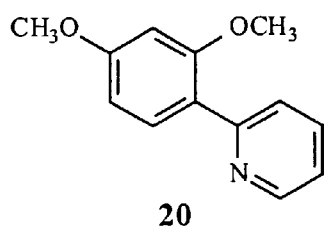
Figure 5:
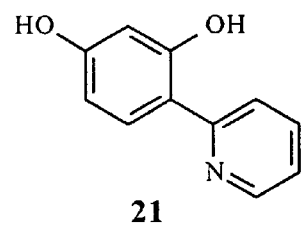
Figure 5:
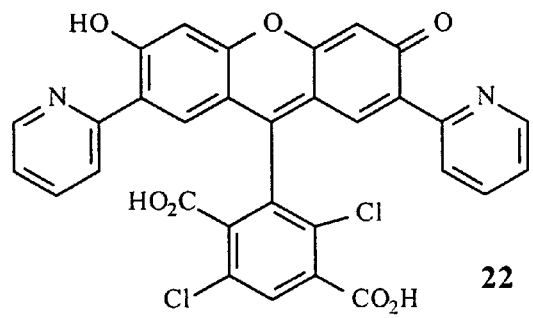
Figure 6:
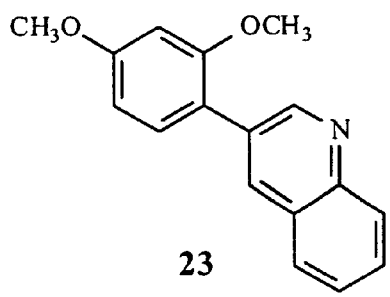
FIG. 6 shows the structures of compounds 23–25
Figure 6:
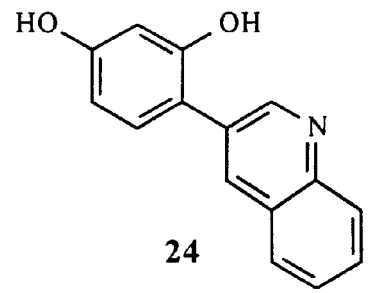
Figure 6:
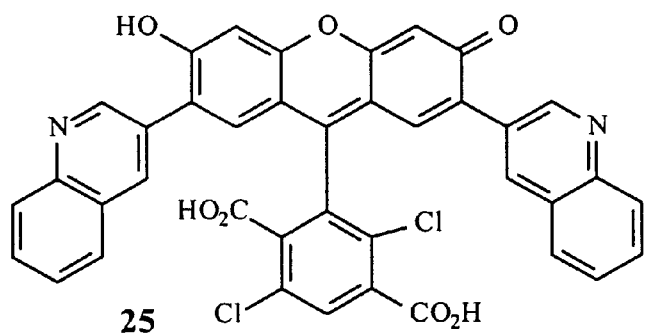
Figure 7:
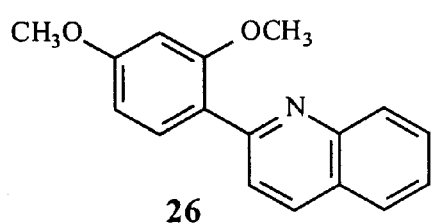
FIG. 7 shows the structures of compounds 26–28
Figure 7:
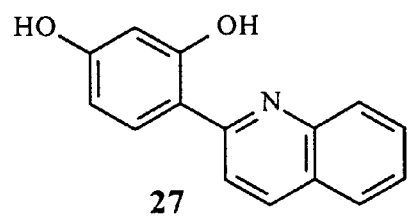
Figure 7:
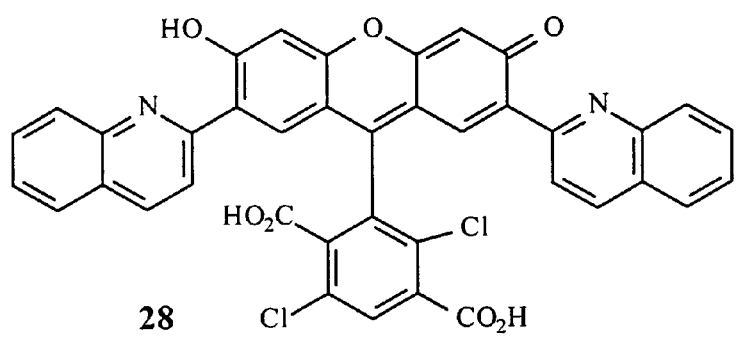
Figure 8:
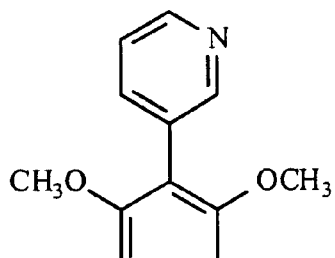
FIG. 8 shows the structures of compounds 29–33
Figure 8:
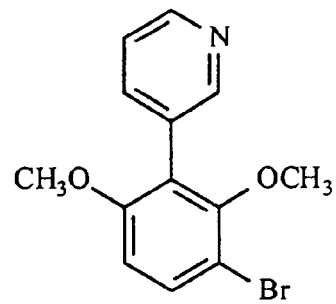
Figure 8:
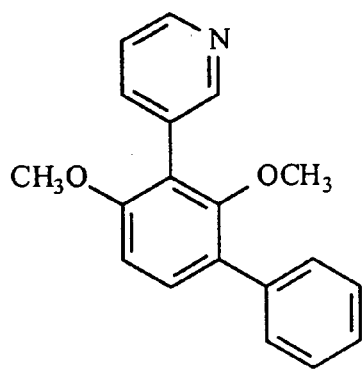
Figure 8:
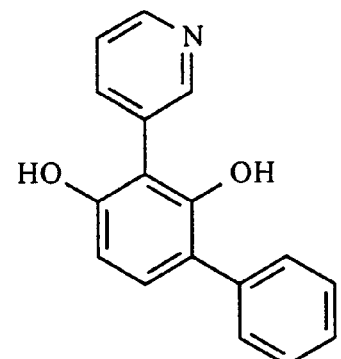
Figure 8:
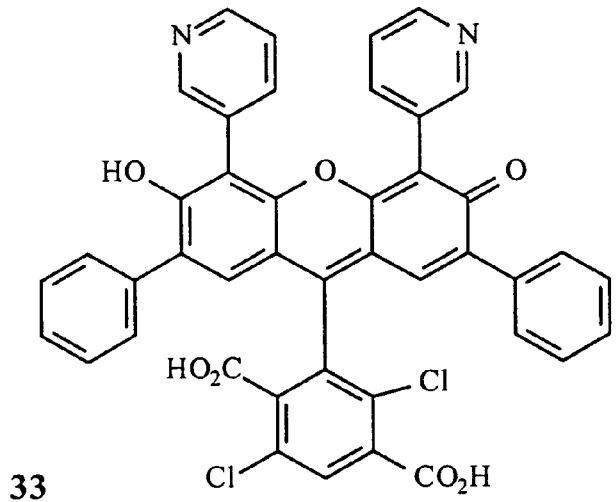
Figure 9:
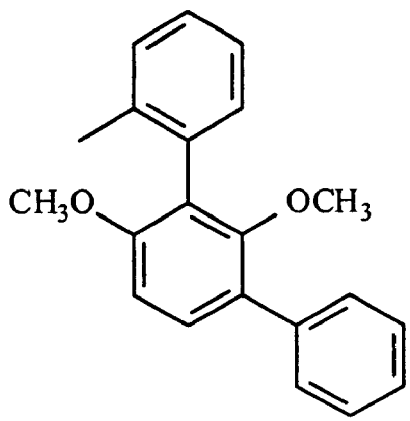
FIG. 9 shows the structures of compounds 34–36
Figure 9:
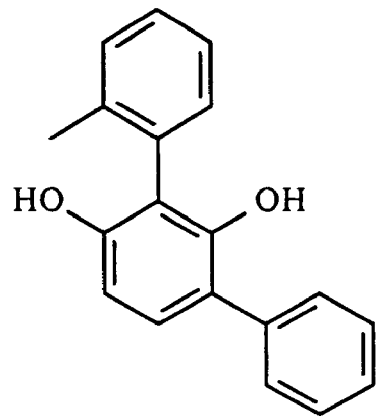
Figure 9:
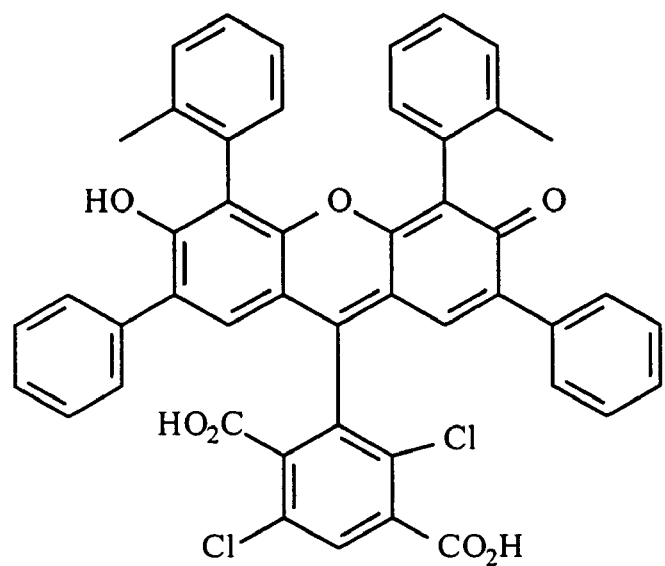
Figure 10:
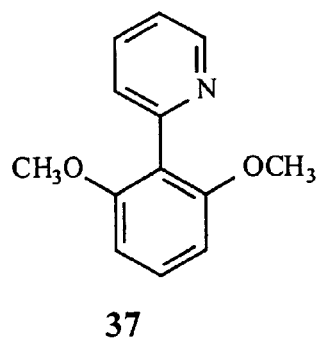
FIG. 10 shows the structures of compounds 37–41
Figure 10:
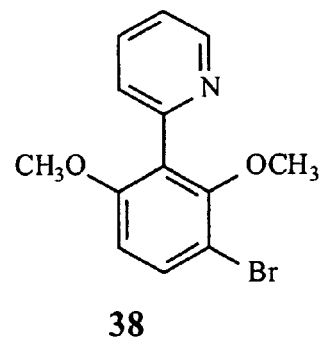
Figure 10:
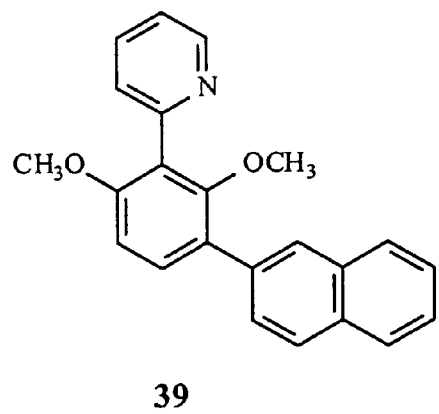
Figure 10:
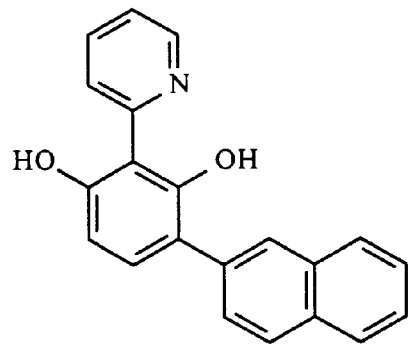
Figure 10:
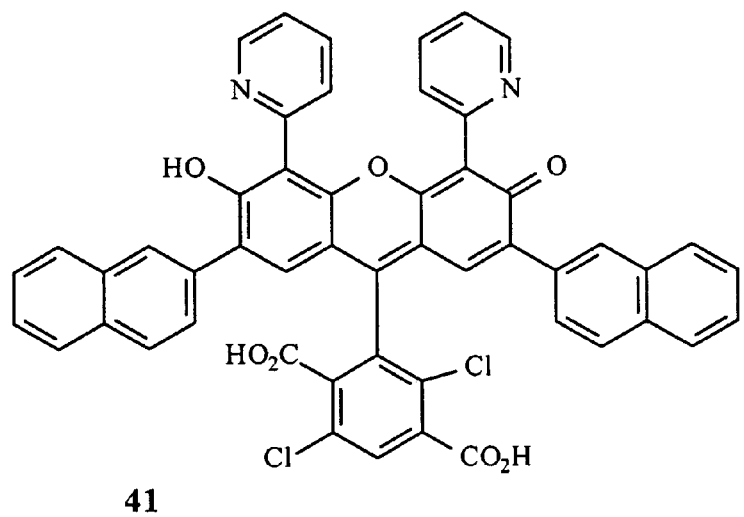

By the same methods, electron-deficient nitrogen heterocycle-substituted fluorescein dyes 19, 22 (FIG. 5), 25 (FIG. 6), 28 (FIG. 7), 33 (FIG. 8), 36 (FIG. 9, and 41 (FIG. 10) were synthesized (Examples 17–41).

Labelling Reagents of the Dyes

The present invention comprises labelling reagents wherein electron-deficient nitrogen heterocycle-substituted fluorescein dyes are in reactive form to react with substrates. In another aspect, the present invention comprises substrates labelled or conjugated with the fluorescein dyes of the invention, i.e. structure I. Substrates can be virtually any molecule or substance to which the dyes of the invention can be conjugated, including by way of example and not limitation, proteins, polypeptides, polysaccharides, nucleosides, nucleotides, polynucleotides, lipids, solid supports, organic and inorganic polymers, and combinations and assemblages thereof, such as chromosomes, nuclei, living cells (e.g., bacteria or other microorganisms, mammalian cells, tissues, etc.), and the like. The dyes are conjugated with the substrate via an optional linker by a variety of means, including hydrophobic attraction, ionic attraction, and covalent attachment. Preferably, the dyes are conjugated to the substrate via covalent attachment.

Labelling typically results from mixing an appropriate reactive fluorescent dye and a substrate to be conjugated in a suitable solvent in which both are soluble, using methods well-known in the art (Hermanson, *Bioconjugate Techniques,* Academic Press, San Diego, Calif. pp. 40–55, 643–71, (1996)), followed by separation of the conjugate from any unconjugated starting materials or unwanted by-products. The dye conjugate can be stored dry or in solution for later use.

The fluorescein dyes of the invention may include a reactive linking group at one of the substituent positions, $R^1$–$R^5$, $R^7$, $X^1$–$X^5$, or covalent attachment of the dye to another molecule, i.e. a substrate. Reactive linking groups are moieties on the dye and on the substrate which are capable of forming a covalent bond. Typically the dye has electrophilic functional group(s) capable of reacting with nucleophilic functional group(s) on the substrate. Examples of substrate nucleophiles include alcohols, alkoxides, amines, hydroxylamines, and thiols. The selection of the reactive linking groups used to attach the dye to the substrate typically depends on the complementary functionality on the substrate to be conjugated. Examples of electrophile reactive linking groups include succinimidyl ester, isothiocyanate, sulfonyl chloride, sulfonate ester, silyl halide, 2,6-dichlorotriazinyl, pentafluorophenyl ester, phosphoramidite, maleimide, haloacetyl, epoxide, alkylhalide, allyl halide, aldehyde, ketone, acylazide, anhydride, and iodoacetamide. A single type of reactive linking group may be available on the substrate (typical for polysaccharides), or a variety of groups may occur (e.g. amines, thiols, alcohols, phenols), as is typical for proteins. A conjugated substrate may be conjugated to more than one dye, which may be the same or different, or to a substrate that is additionally modified by a hapten. Although some selectivity can be obtained by careful control of the reaction conditions, selectivity of labelling is best obtained by selection of an appropriate reactive dye.

A preferred reactive linking group is N-hydroxysuccinimidyl ester (NHS) of a carboxyl group substituent of the fluorescein dye. The NHS ester form of the dye is a preferred labelling reagent. The NHS ester of the dye may be preformed, isolated, purified, and/or characterized, or it may be formed in situ and reacted with a nucleophilic group of a substrate, such as an oligonucleotide, a nucleotide, a peptide, or the like. Typically, the carboxyl form of the dyes of the present invention, e.g. the dye compounds of Table 1, are reacted with a carbodiimide reagent, e.g. dicyclohexylcarbodiimide, diisopropylcarbodiimide, or a uronium reagent, e.g. HBTU (O-benzotriazol-1-yl)-N,N,N',N'-tetramethyluronium hexafluorophosphate) or HATU (O-(7-azabenzotriazol-1-yl)-N,N,N',N'-tetramethyluronium hexafluorophosphate), and an activator, such as 1-hydroxybenzotriazole (HOBt), and N-hydroxysuccinimide to give the NHS ester of the dye.

Preferred substituent positions for NHS esters on the fluorescein dyes of the invention are $X^3$ and $X^4$ (Ia). A representative example of an NHS ester is structure Ib:

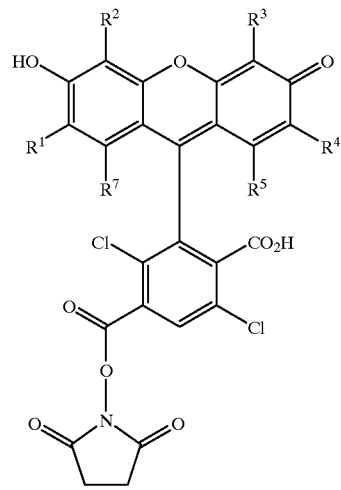

Another preferred reactive linking group is a phosphoramidite form of the dyes of the present invention. Phosphoramidite dye reagents are particularly useful for the automated synthesis of oligonucleotides labelled with the dyes of the invention. Oligonucleotides are commonly synthesized on solid supports by the phosphoramidite method using phosphoramidite nucleoside reagents (Caruthers, M. and Beaucage, S. "Phosphoramidite compounds and processes", U.S. Pat. No. 4,415,732, issued Nov. 15, 1983; Caruthers, M. and Matteucci, M. "Process for preparing polynucleotides", U.S. Pat. No. 4,458,066, issued Jul. 3, 1984; Beaucage, S. and Iyer, R. (1992) "Advances in the synthesis of oligonucleotides by the phosphoramidite approach", Tetrahedron 48:2223–2311). The phosphoramidite dye reagents can be nucleosidic or non-nucleosidic, and can be conveniently used to label synthetic polynucleotides or polynucleotide analogs at their 3'-terminus, 5'-terminus and/or at one or more internal positions. Non-nucleosidic forms of phosphoramidite dye reagents have the general structure III

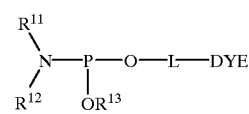

where DYE is a protected or unprotected form of dye I, including energy transfer dye. L is a linker. $R^{11}$ and $R^{12}$ taken separately are alkyl ($C_1$–$C_{12}$), alkene, aryl, and cycloalkyl containing up to 10 carbon atoms, or $R^{11}$ and $R^{12}$ taken together with the nitrogen atom form a saturated nitrogen heterocycle. $R^{13}$ is a phosphite ester protecting group which prevents unwanted extension of the oligonucleotide. Generally, $R^{13}$ is stable to oligonucleotide synthesis conditions yet is able to be removed from a synthetic oligonucleotide product with a reagent that does not adversely affect the integrity of the oligonucleotide or the dye. A variety of phosphite ester groups having these characteristics are well-known in the art. Preferably, $R^{13}$ is methyl; 2-cyanoethyl, —$CH_2CH_2CN$; and 2-(4-nitrophenyl) ethyl, —$CH_2CH_2(p\text{-}NO_2Ph)$. Preferred embodiments of phosphoramidite dye reagents are where: (i) $R^{11}$ and $R^{12}$ are each isopropyl, (ii) $R^{11}$ and $R^{12}$ taken together is morpholino, (iii) L is alkyl ($C_1$–$C_{12}$), (iv) $R^{13}$ is 2-cyanoethyl, and (v) DYE is attached at $R^6$ by a linker. Phosphoramidite dye reagents III effect labelling of a substrate with a single fluorescent dye of the invention. Where the substrate is an oligonucleotide, the dye will be attached at the 5' terminus of the oligonucleotide, as a consequence of the 3' to 5' direction of synthesis. Other phosphoramidite dye reagents, nucleosidic and non-nucleosidic allow for labelling at other sites of an oligonucleotide, e.g. 3' terminus, nucleobase, internucleotide linkage, sugar. Labelling at the nucleobase, internucleotide linkage, and sugar sites allows for internal and multiple labelling with fluorescent dyes.

When reacted with a hydroxyl group, e.g. 5' terminal OH of an oligonucleotide bound to a solid support, and under mild acid activation, the phosphoramidite dye reagent III reacts to form an internucleotide phosphite group which is then oxidized to an internucleotide phosphate group. In some instances, the dye may contain functional groups, e.g. phenolic oxygens as in structure I, that require protection either during the synthesis of the phosphoramidite dye reagent or during its subsequent use to label molecules such as oligonucleotides. The protecting group(s) used will depend upon the nature of the functional groups, and will be apparent to those having skill in the art (Greene, T. and Wuts, P. *Protective Groups in Organic Synthesis*, 2nd Ed., John Wiley & Sons, New York, 1991). Generally, the protecting groups used should be stable under the acidic conditions (e.g. trichloroacetic acid, dichloroacetic acid) commonly employed in oligonucleotide synthesis to remove 5'-hydroxyl protecting groups (e.g., dimethoxytrityl) and labile under the basic conditions (ammonium hydroxide, aqueous methylamine) used to deprotect and/or cleave synthetic oligonucleotides from solid supports.

Stable phosphoramidite dye reagents may be formed by initial protection of the xanthene ring oxygens of structure I, typically esterification, e.g. acylation as pivalate (R=tBu) or benzoate (R=Ph) esters. Esterification causes lactonization of structures Ia which renders the reagent in the non-fluorescent, protected state, e.g. structure Ic:

Ic

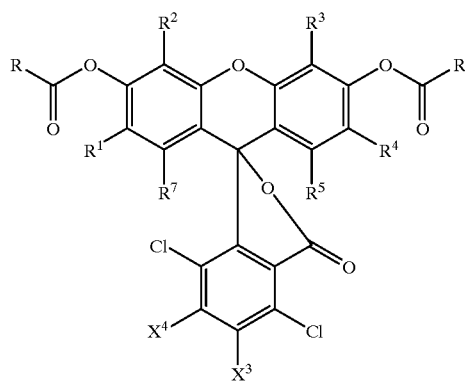

Where one of $X^3$ and $X^4$ is hydrogen and the other is carboxyl, the dye may be converted to a non-nucleosidic, phosphoramidite dye labelling reagent, e.g. Id, by known reactions, such as activation of the carboxyl, amidation with 6-amino, 1-hexanol and phosphitylation of hydroxyl with bis(diisopropylamino)cyanoethylphosphite (Theisen, etal (1992) "Fluorescent dye phosphoramidite labelling of oligonucleotides", in *Nucleic Acid Symposium Series* No. 27, Oxford University Press, Oxford, pp. 99–100).

Id

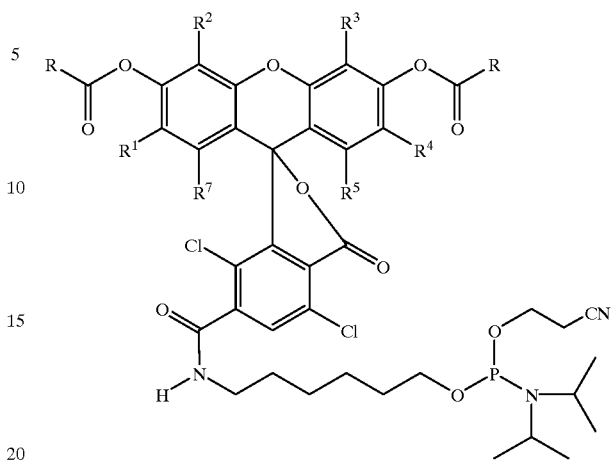

Dyes of the invention may also be covalently attached to solid supports for the automated synthesis of oligonucleotides (Mullah, B. and Andrus, A. "Solid support reagents for the direct synthesis of 3'-labelled polynucleotides", U.S. Pat. No. 5,736,626, issued Apr. 7, 1998; Caruthers, M. and Matteucci, M. "Process for preparing polynucleotides", U.S. Pat. No. 4,458,066, issued Jul. 3, 1984). In one embodiment, the dye is attached to a linker that has an attachment to a solid support, e.g. controlled-pore-glass (Nelson, etal (1992) "Oligonucleotide labeling methods 3. Direct labeling of oligonucleotides employing a novel, non-nucleosidic, 2-aminobutyl-1,3-propanediol backbone", Nucl. Acids Res. 20:6253–59; Nelson, P. "Multifunctional controlled pore glass reagent for solid phase oligonucleotide synthesis", U.S. Pat. No. 5,141,813, issued Aug. 25, 1992) or polystyrene (Andrus, etal "Automated system for polynucleotide synthesis and purification", U.S. Pat. No. 5,047,524, issued Sep. 10, 1991 and U.S. Pat. No. 5,262,530, issued Nov. 16, 1993), and acid-labile functionality for extension with phosphoramidite nucleoside reagents. After cleavage and deprotection, the labelled oligonucleotide may bear a dye of the present invention at the 3' terminus.

Nucleotide Labelling

A preferred class of labelled substrates include conjugates of nucleosides and nucleotides that are labelled with the fluorescein dyes of the invention. Such labelled nucleosides and nucleotides are particularly useful for labelling polynucleotides formed by enzymatic synthesis, e.g., labelled nucleotide 5'-triphosphates used in the context of PCR amplification, Sanger-type polynucleotide sequencing, and nick-translation reactions.

The dye may be conjugated to either the sugar or nucleobase. In a preferred embodiment, the compound is a terminating ribonucleoside-5'-triphosphate, "terminator", in which the dye is covalently attached to the nucleobase moiety. When used in conjunction with 2'-deoxyribonucleoside-5'-triphosphates, "dNTP" or ribonucleoside-5'-triphosphates, "NTP", appropriate polymerase enzymes and primed target polynucleotides, such terminators can be used to generate series of terminated electron deficient nitrogen heterocycle-substituted fluorescein dye labelled polynucleotide fragments via target-mediated enzymatic synthesis for applications such as DNA sequencing. Nucleosides and nucleotides can be labelled at sites on the sugar or nucleobase moieties. Preferred nucleobase labelling sites include the 8-C of a purine nucleobase, the 7-C or 8-C of a 7-deazapurine nucleobase, and the 5-position of a pyrimidine nucleobase. Between a nucleoside or nucleotide and a dye, a linker may attach to a dye at any one of positions $R^1$–$R^7$.

The labelled nucleoside or nucleotide may be enzymatically incorporatable and enzymatically extendable. Nucleosides or nucleotides labelled with dyes of the present invention may have structure IV:

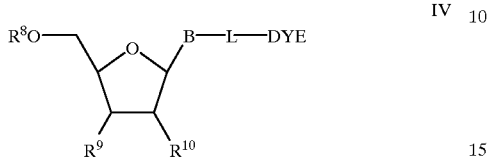

IV where DYE is a protected or unprotected form of dye I, including energy transfer dye. B is a nucleobase, e.g. uracil, thymine, cytosine, adenine, 7-deazaadenine, guanine, and 8-deazaguanosine. $R^8$ is H, monophosphate, diphosphate, triphosphate, thiophosphate, or phosphate analog. $R^9$ and $R^{10}$, when taken alone, are each independently H, HO, F. Where the labelled nucleoside or nucleotide is a terminator, $R^9$ and $R^{10}$ are selected to block polymerase-mediated target-directed polymerization. In terminator nucleotides, $R^9$ and $R^{10}$, when taken alone, are each independently H, F, and a moiety which blocks polymerase-mediated target-directed polymerization, or when taken together form 2'-3'-didehydroribose.

Linker L may be:

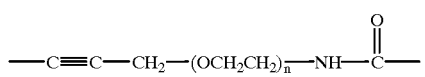

wherein n is 0, 1, or 2.

Oligonucleotide Labelling

Another preferred class of labelled substrates include conjugates of oligonucleotides that are labelled with the fluorescein dyes of the invention. Such labelled polynucleotides or analogs are useful in a number of important contexts, including as DNA sequencing primers, PCR primers, oligonucleotide hybridization probes, oligonucleotide ligation probes, double-labelled 5'-exonuclease (TaqMan™) probes, and the like (Fung, etal. "Amino-derivatized phosphite and phosphate linking agents, phosphoramidite precursors, and useful conjugates thereof", U.S. Pat. No. 4,757,141, issued Jul. 12, 1988; Andrus, A. "Chemical methods for 5' non-isotopic labelling of PCR probes and primers" (1995) in PCR 2: *A Practical Approach*, Oxford University Press, Oxford, pp. 39–54; Hermanson, (1996) *Bioconjugate Techniques*, Academic Press, San Diego, Calif. pp. 40–55, 643–71). A labelled oligonucleotide may have structure V:

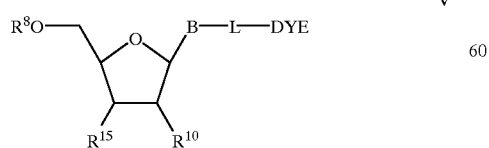

V where the oligonucleotide comprises 2 to 100 nucleotides. DYE is a fluorescent dye I, including energy transfer dye. B is a nucleobase, e.g. uracil, thymine, cytosine, adenine, 7-deazaadenine, guanine, and 8-deazaguanosine. L is a linker. $R^{10}$ is H, OH, halide, azide, amine, alkylamine, alkyl ($C^1$–$C_6$), allyl, alkoxy ($C_1$–$C_6$), $OCH_3$, or $OCH_2CH=CH_2$. $R^{15}$ is H, phosphate, internucleotide phosphodiester, or internucleotide analog. $R^{16}$ is H, phosphate, internucleotide phosphodiester, or internucleotide analog. In this embodiment, structure V, the nucleobase-labelled oligonucleotide may bear multiple dyes of the invention attached through the nucleobases.

Nucleobase-labelled oligonucleotide V may be formed by: (i) enzymatic incorporation of enzymatically incorporatable nucleotide reagents IV where $R^8$ is triphosphate, by a DNA polymerase or ligase, and (ii) coupling of phosphoramidite dye nucleoside reagent VI by automated synthesis.

Generally, if the labelled oligonucleotide is made by enzymatic synthesis, the following procedure may be used. A target DNA is denatured and an oligonucleotide primer is annealed to the target DNA. A mixture of enzymatically-incorporatable nucleotides or nucleotide analogs capable of supporting continuous target-directed enzymatic extension of the primed target (e.g., a mixture including dGTP, dATP, dCTP and dTTP or dUTP) is added to the primed target. At least a fraction of the nucleotides is labelled with a dye I or are labelled terminators, as described above. Next, a polymerase enzyme is added to the mixture under conditions where the polymerase enzyme is active. A labelled oligonucleotide is formed by the incorporation of the labelled nucleotides or terminators during polymerase-mediated strand synthesis.

In an alternative enzymatic synthesis method, two primers are used instead of one: one complementary to the (+) strand of the target sequence and another complementary to the (−) strand of the target sequence, the polymerase is a thermostable polymerase and the reaction temperature is cycled between a denaturation temperature and an extension temperature, thereby exponentially amplifying a labelled complement to the target sequence by PCR (Innis, etal (1990) *PCR Protocols*, Eds., Academic Press). One or both primers may be labelled with a dye of the invention. Alternatively, one or more of the nucleotide 5'-triphosphates may be labelled with a dye of the invention. Each labelling scheme results in a DNA amplification product bearing one or more dyes of the invention.

Internal labelling of oligonucleotides with fluorescent dyes of the inventions can be conducted with nucleoside phosphoramidite dye reagents of general structure VI:

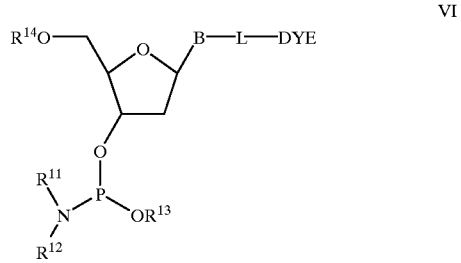

VI where DYE is a protected or unprotected form of dye I. The exocyclic amines and other functionalities of nucleobase B may require protection during the synthesis of the nucleoside phosphoramidite dye reagent and/or during its subsequent use to synthesize labelled oligonucleotides. The particular protecting group(s) selected will depend on the identity of the nucleobase or nucleobase analog, and will be apparent to those of skill in the art. For example, the exocyclic amines of adenine and cytosine can be protected with benzoyl (bz) and the exocyclic amine of guanine can be protected with dimethylformamide (dmf) or isobutyryl (ibu) using conventional procedures. Preferably, the nucleobase is protected with groups that are readily removed under mild basic conditions. For example, oligonucleotides synthesized with $dA^{bz}$, $dC^{bz}$, $dG^{dmf}$ and T phosphoramidite nucleosides (and their corresponding 3' nucleoside solid supports) can be cleaved and deprotected in 60 minutes in concentrated ammonium hydroxide at 65° C. (Beaucage, S. and Iyer, R. (1992) "Advances in the synthesis of oligonucleotides by the phosphoramidite approach", Tetrahedron 48:2223–2311).

$R^{11}$ and $R^{12}$ taken separately are selected from the group consisting of alkyl ($C_1$–$C_6$), alkene, aryl, and cycloalkyl containing up to 10 carbon atoms, e.g. isopropyl, or $R^{11}$ and $R^{12}$ taken together with the nitrogen atom form a saturated nitrogen heterocycle, e.g. morpholino. $R^{13}$ is a phosphite ester protecting group, e.g. methyl, 2-cyanoethyl, and 2-(4-nitrophenyl)ethyl. $R^{14}$ is an acid-cleavable hydroxyl protecting group, e.g. dimethoxytrityl, which allows subsequent monomer coupling.

The linker L of VI may be

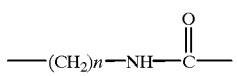

wherein n ranges from 2 to 10;

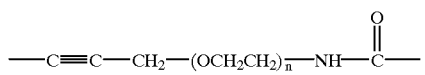

wherein n is 0, 1, or 2; and

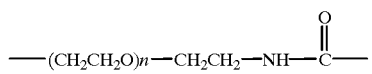

wherein n ranges from 1 to 10.

Reagents IV and VI are effective in preparing oligonucleotides V labelled with the dyes of the invention I. Another embodiment of a labelled oligonucleotide is 5' terminus labelled according to structure VII:

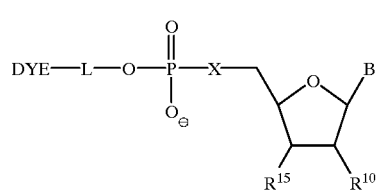

VII where X is O, NH, or S, L is alkyldiyl ($C_1$–$C_{12}$) or mobility-modifier, and the labelled oligonucleotide bears only one DYE. Mobility-modifier linkers affect the electrophoretic mobility or hydrophobic properties of the oligonucleotide. Examples of mobility-modifier linkers include ethyleneoxy units, —$(CH_2CH_2O)_n$—, where n maybe 1 to 100 (Grossman, etal "Method of DNA sequencing employing a mixed DNA-polymer chain probe", U.S. Pat. No. 5,624,800, Issued Apr. 29, 1997). Preferably, n is from 2 to 20. Labelled oligonucleotide VII may be formed by automated synthesis with phosphoramidite reagents III, in particular for example Id. Alternatively, labelled oligonucleotides VII may be formed by reacting a reactive linking group form of a dye of the present invention, e.g. Ib, with a 5'-aminoalkyl oligonucleotide.

In one preferred post-synthesis chemical labelling method an oligonucleotide is labelled as follows. A dye according to structure Ib is dissolved or suspended in DMSO and added in excess (10–20×) to a 5'-aminohexyl oligonucleotide in 0.25 M bicarbonate/carbonate buffer at about pH 9 and allowed to react for 6 hours, e.g. U.S. Pat. No. 4,757,141. The dye labelled oligonucleotide VII can be separated from unreacted dye by passage through a size-exclusion chromatography column eluting with buffer, e.g., 0.1 molar triethylamine acetate (TEAA). The fraction containing the crude labelled oligonucleotide VII, where L is —$(CH_2)_6$—, is further purified by reverse phase HPLC employing gradient elution.

Kits

The invention comprises kits comprising the electron-deficient nitrogen heterocycle-substituted fluorescein dyes of the invention and/or their labelled conjugates. In one embodiment, the kits are useful for conjugating the dyes of the invention to other molecules, i.e. substrates. Such kits generally comprise a dye of the invention including an optional linking moiety and reagents, enzymes, buffers, solvents, etc. suitable for conjugating the dye to another molecule or substance.

In one embodiment, the kits are useful for labelling enzymatically synthesized oligonucleotides and polynucleotides with the dyes of the invention. Such kits generally comprise a labelled enzymatically-incorporatable nucleotide or nucleotide analog according to the invention, a mixture of enzymatically-incorporatable nucleotides or nucleotide analogs capable of supporting continuous primer extension and a polymerase enzyme. Preferably, the labelled enzymatically-incorporatable nucleotide or nucleotide analog is a compound according to structure IV, most preferably a labelled terminator. Preferred polymerases are thermostable, such as AMPLITAQ® DNA polymerase FA (PE Biosystems, Foster City, Calif.).

In another embodiment, the kits are useful for labelling synthetic oligonucleotides with the phosphoramidite dye reagents of the invention. Such kits generally comprise a phosphoramidite dye reagent, other synthesis reagents, and/or solid supports optionally for carrying out oligonucleotide synthesis (Andrus, etal "Automated system for polynucleotide synthesis and purification" U.S. Pat. No. 5,262,530, issued Nov. 16, 1993).

Methods Using Labelled Reagents

The dyes and reagents of the present invention are well suited to any method utilizing fluorescent detection, particularly methods requiring the simultaneous detection of multiple spatially-overlapping analytes (Menchen, etal "4,7-dichlorofluorescein dyes as molecular probes", U.S. Pat. No. 5,188,934, issued Feb. 23, 1993. Dyes and reagents of the invention are particularly well suited for identifying classes of polynucleotides that have been subjected to a biochemical separation procedure, such as electrophoresis, or that have been distributed among locations in a spatially-addressable hybridization array.

These applications include use of the labelled oligonucleotides as 5'-labelled sequencing primers, 5'-labelled polymerase chain reaction (PCR) primers, hybridization probes, and ligation assay probes. PCR applications include the use of labelled oligonucleotides for genotyping by variable number tandem repeat (VNTR), short tandem repeat (STR), and microsatellite methods of amplification of repeat regions of double-stranded DNA that contain adjacent multiple copies of a particular sequence, with the number of repeating units being variable. Preferably, in such PCR genotyping methods, the PCR primer is labelled with a dye of the invention.

In a particularly preferred embodiment, the fluorescein dyes of the invention may be used in quantitative methods and reagents that provide real time or end-point measurements of amplification products during PCR (Gelfand, etal. "Homogeneous assay system using the nuclease activity of a nucleic acid polymerase", U.S. Pat. No. 5,210,015, issued May 9, 1993; Livak, etal "Method for Detecting Nucleic Acid Amplification Using Self-Quenching Fluorescence Probe", U.S. Pat. No. 5,538,848, issued Jul. 23, 1996). The exonuclease assay (Taqman®) employing fluorescent dye-quencher probes (Livak, etal "Self-quenching fluorescence probe", U.S. Pat. No. 5,723,591, issued Mar. 3, 1998; Mullah, etal (1998) "Efficient synthesis of double dye-labelled oligodeoxyribonucleotide probes and their application in a real time PCR assay", Nucl. Acids Res. 26:1026–1031) gives direct detection of polymerase chain reaction (PCR) products in a closed-tube system, with no sample processing beyond that required to perform the PCR. In the Taqman assay, the polymerase that conducts primer extension and amplifies the polynucleotide also displaces and cleaves a probe annealed to target sequence by 5' to 3' exonuclease activity. In a Taqman-type assay, the probe is self-quenching, labelled with fluorescent dye and quencher moieties, either of which may be dyes of the invention. Spectral overlap allows for efficient energy transfer (FRET) when the probe is intact (Clegg, R. (1992) "Fluorescence resonance energy transfer and nucleic acids", Meth. Enzymol. 211:353–388). When hybridized to a target sequence, the probe is cleaved during PCR to release a fluorescent signal that is proportional to the amount of target-probe hybrid present (Livak, etal "Method for Detecting Nucleic Acid Amplification Using Self-Quenching Fluorescence Probe", U.S. Pat. No. 5,538,848, issued Jul. 23, 1996; Livak, etal "Self-quenching fluorescence probe", U.S. Pat. No. 5,723,591, issued Mar. 3, 1998).

In yet another aspect, the invention provides methods of using the electron deficient nitrogen heterocycle-substituted fluorescein dyes of the invention to sequence a target polynucleotide. The method generally comprises forming a series of differently-sized polynucleotides labelled with a dye of the invention, separating the series of differently-sized labelled polynucleotides based on size and detecting the separated labelled polynucleotides based on the fluorescence of the dye.

The series of differently-sized labelled polynucleotides can be conveniently generated by enzymatically extending a primed target sequence according to well-known methods (Sanger, etal, (1977) "DNA sequencing with chain-terminating inhibitors", Proc. Natl. Acad. Sci. USA 74:5463–5467; Hunkapiller, etal "Real time scanning electrophoresis apparatus for DNA sequencing", U.S. Pat. No. 4,811,218, issued Mar. 7, 1989; PE Corp., Jan. 1995, *ABI PRISM® 377 DNA Sequencer User's Manual, Rev. A*, Chapter 2 (P/N 903433, PE Corporation, Foster City, Calif.). For example, the series of labelled polynucleotides can be obtained using a labelled primer and enzymatically extending target sequence primed with the labelled target in the presence of a polymerase, dNTP, and at least one terminator (e.g., 2',3'-dideoxyribonucleoside-5'-triphosphate). Alternatively, the series of labelled polynucleotides can be obtained by enzymatically extending an unlabelled primed target in the presence of a polymerase, dNTP and at least one labelled terminator (Bergot, etal "Spectrally resolvable rhodamine dyes for nucleic acid sequence determination", U.S. Pat. No. 5,366,860, issued Nov. 22, 1994). In either embodiment, the polymerase serves to extend the primer with dNTP until a terminator is incorporated, which terminates the extension reaction. Once terminated, the series of labelled polynucleotides are separated based on size and the separated polynucleotides are detected based on the fluorescence of the dye labels.

In a particularly advantageous embodiment of this method, four different fluorescently labelled terminators are used, where each nucleoside is labelled with a different spectrally-resolvable fluorophore, and at least one of the fluorophores is an electron deficient nitrogen heterocycle-substituted fluorescein dye according to the invention such that the set of fluorophores are "mobility matched." According to this embodiment, the primed target sequence is enzymatically extended in the presence of a polymerase, dNTP and the four different fluorescently labelled terminators. Following separation based on size, a series of separated labelled polynucleotides is obtained in which the emission properties of the fluorescent dye reveal the identity of the 3'-terminal nucleotide. In a particularly preferred embodiment, all of the fluorescent dyes of the mobility matched set are excitable using a single light source.

In a preferred category of methods referred to herein as "fragment analysis" or "genetic analysis" methods, labelled polynucleotide sequences, or "fragments" are generated through target-directed enzymatic synthesis using labelled primers or nucleotides, e.g. by ligation or polymerase-directed primer extension; the fragments are subjected to a size-dependent separation process, e.g., electrophoresis or chromatography; and the separated fragments are detected subsequent to the separation, e.g., by laser-induced fluorescence (Hunkapiller, etal "Real time scanning electrophoresis apparatus for DNA sequencing", U.S. Pat. No. 4,811,218, issued Mar. 7, 1989). In a particularly preferred embodiment, multiple classes of polynucleotides are separated simultaneously and the different classes are distinguished by spectrally resolvable labels.

In a particularly preferred fragment analysis method, fragments labelled with dyes of the invention are identified by relative size. Correspondence between fragment size and sequence is established by incorporation of the four possible terminating bases ("terminators") and the members of a set of spectrally resolvable dyes. Such sets are readily assembled from the dyes of the invention by measuring emission and absorption bandwidths with commercially available spectrophotometers. Preferably, the chain termination methods of DNA sequencing, i.e. dideoxy DNA sequencing, or Sanger-type sequencing, and fragment analysis is employed. Each of the terminators bears a different fluorescent dye and collectively the terminators of the experiment bear a set of dyes including one or more from the dyes of the invention.

Spectrally-resolvable fluorescent dyes of the invention are also useful in genotyping experiments after PCR amplification of target. In particular, a set of primer oligonucleotides, labelled at the 5' terminus, each with different dyes, can amplify multiple loci and discriminate single nucleotide polymorphisms (SNP). Electrophoretic separation of the dye labelled amplification products, with size standards, establishes a profile or characteristic data set indicating a certain genotype dependent on the set of primer sequences.

The covalent joining of polynucleotide probes by ligase enzymes is one of the most useful tools available to molecular biologists. When two probes are annealed to a target sequence where the two probes are adjacent and without intervening gaps, a phosphodiester bond can be formed between a 5' terminus of one probe and the 3' terminus of the other probe by a ligase enzyme, (Whiteley, etal "Detection of specific sequences in nucleic acids", U.S. Pat. No. 4,883, 750, issued 1989; Landegren, etal. (1988) "A ligase mediated gene detection technique", Science 241:1077–80; Nickerson, etal (1990) "Automated DNA diagnostics using an ELISA-based oligonucleotide assay" Proc. Natl. Acad. Sci USA 87:8923–27). Oligonucleotide ligation assays detect the presence of specific sequences in a target sample. Where one or both probes are labelled with a dye of the invention, the ligation product may be detected by fluorescence (Grossman, etal (1994) "High-density multiplex detection of nucleic acid sequences: oligonucleotide ligation assay and sequence-coded separation", Nucl. Acids Res. 22:4527–34).

Sanger-type sequencing involves the synthesis of a DNA strand by a DNA polymerase in vitro using a single-stranded or double-stranded DNA target whose sequence is to be determined. Synthesis is initiated at a defined site based on where an oligonucleotide primer anneals to the target. The synthesis reaction is terminated by incorporation of a nucleotide analog that will not support continued DNA elongation. Exemplary chain-terminating nucleotide analogs include the 2',3'-dideoxynucleoside 5'-triphosphates (ddNTP) which lack the 3'-OH group necessary for 3' to 5' DNA chain elongation. When proper proportions of dNTP (2'-deoxynucleoside 5'-triphosphates) and one of the four ddNTP are used, enzyme-catalyzed polymerization will be terminated in a fraction of the population of chains at each site where the ddNTP is incorporated. If fluorescent dye-labelled primers or labelled ddNTP are used for each reaction, the sequence information can be detected by fluorescence after separation by high-resolution electrophoresis. In the chain termination method, dyes of the invention can be attached to either sequencing primers or dideoxynucleotides. Dyes can be linked to a complementary functionality on the 5' terminus of the primer (Fung, etal "Amino-derivatized phosphite and phosphate linking agents, phosphoramidite precursors, and useful conjugates thereof", U.S. Pat. No. 4,757,141, issued Jul. 12, 1988), on the nucleobase of a primer; or on the nucleobase of a dideoxynucleotide, e.g. via alkynylamino linking groups (Khan, etal "Substituted propargylethoxyamido nucleosides, oligonucleotides and methods for using same", U.S. Pat. No. 5,770,716, issued Jun. 23, 1998, and U.S. Pat. No. 5,821,356, issued Oct. 13, 1998; Hobbs, F. and Trainor, G. "Alkynylamino-nucleotides", U.S. Pat. No. 5,151,507, issued Sep. 29, 1992).

Figure 16:
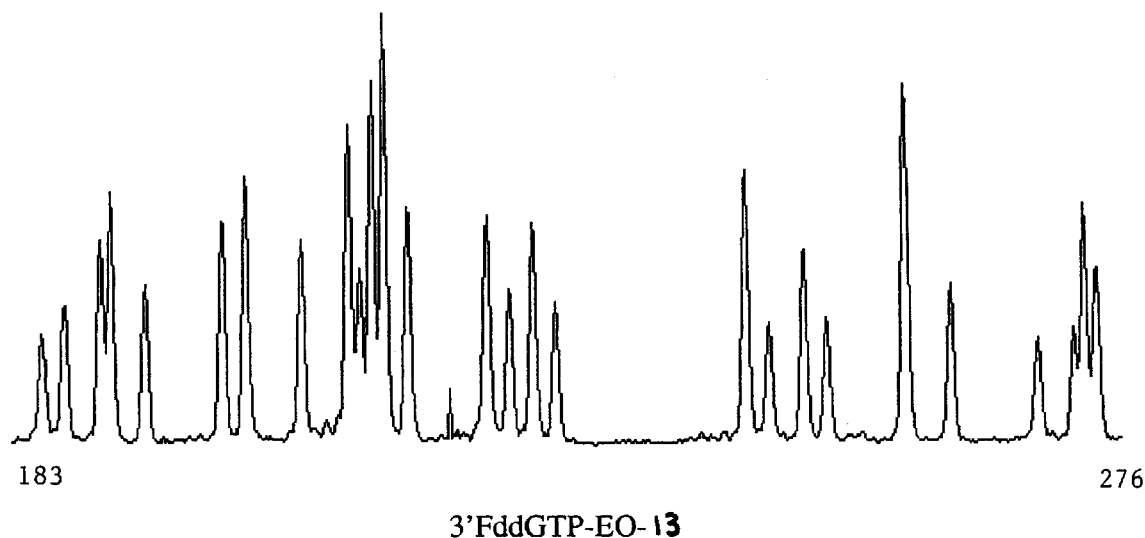
FIG. 16 shows fluorescent detection of labelled sequencing fragments from the ABI PRISM 310. Base 183 to base 276 region from G termination sequence of pGEM target using −21M13 forward primer. Reagents: POP6 electrophoresis medium, Taq FS polymerase, dNTP mix 25 pmole each dATP, dCTP, dITP, dTTP. Top panel: dNTP mix and terminator 3'FddGTP-EO-13. Bottom panel: dNTP mix and energy-transfer dye terminator 3'FddGTP-EO-6FAM-Bn-dR110.
Figure 16:
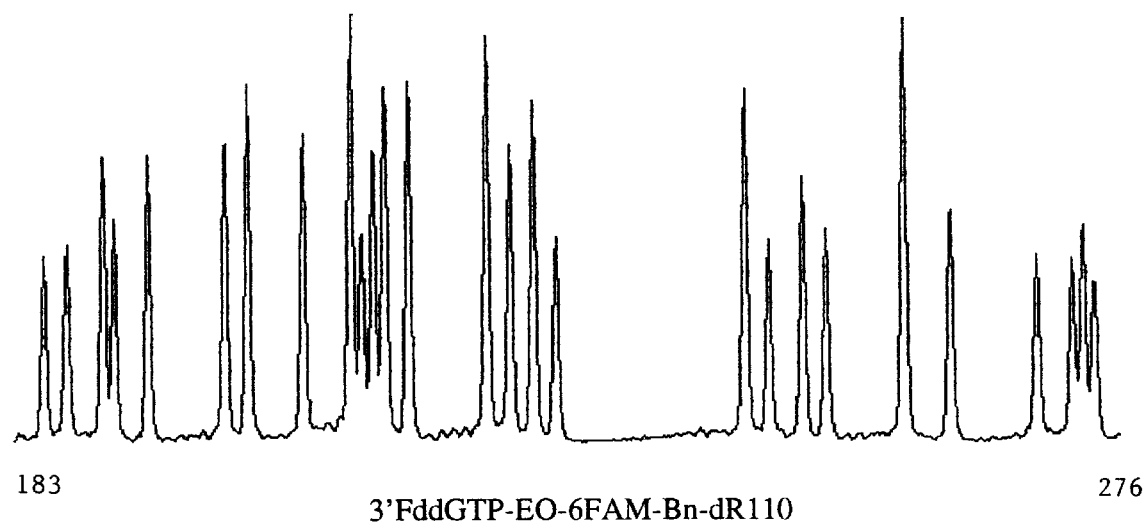

A typical sequencing test is illustrated in FIG. 16 where a 3'-fluoro terminator is labelled with dye compound 13 through a propargylethoxyamido linker (EO): 3'FddGTP-EO-13:

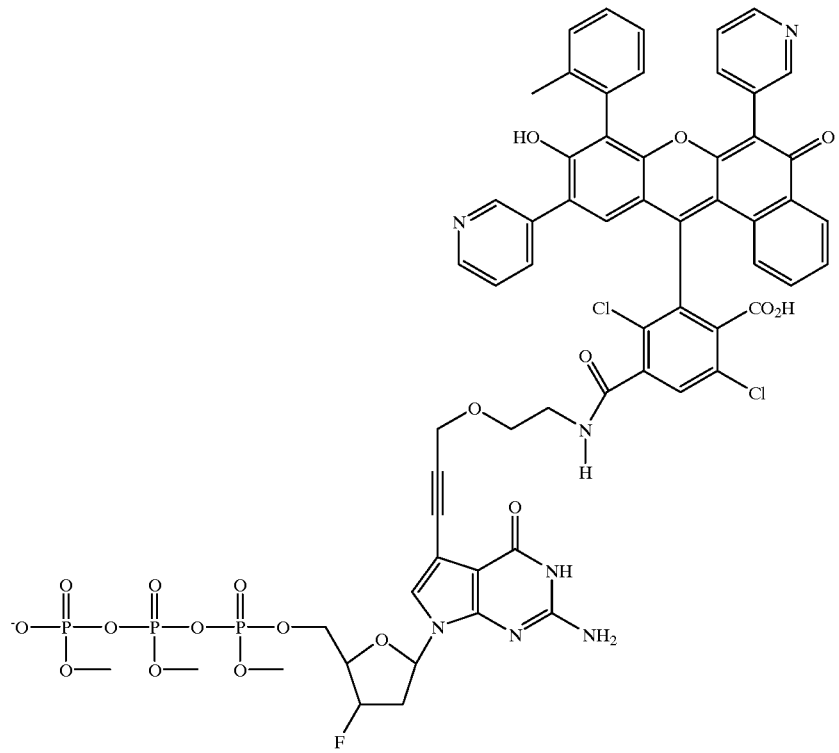

In the above fragment analysis methods, labelled polynucleotides are separated by chromatographic, affinity, or electrophoretic procedures. Preferably the separation is electrophoresis (Rickwood and Hames, Eds., *Gel Electrophoresis of Nucleic Acids: A Practical Approach*, IRL Press Limited, London, 1981). The preferred type of electrophoretic matrix is crosslinked or uncrosslinked polyacrylamide, or other amide-containing polymer, having a concentration (weight to volume) of between about 2–20 weight percent (Madabhushi, etal "Polymers for separation of biomolecules by capillary electrophoresis", U.S. Pat. No.

5,552,028, Issued Sep. 3, 1996). The electrophoretic matrix maybe configured in a slab gel or capillary format (Mathies, etal "Capillary array confocal fluorescence scanner and method", U.S. Pat. No. 5,274,240, issued Dec. 28, 1993). More preferably, the polyacrylamide concentration is between about 4–8 percent. Preferably in the context of DNA sequencing in particular, the electrophoresis matrix includes a denaturing agent, e.g., urea, formamide, and the like (Maniatis etal., *Molecular Cloning: A Laboratory Manual,* Cold Spring Harbor Laboratory, New York, pgs. 179–185 (1982); PE Corp., *ABI PRISM® 377 DNA Sequencer User's Manual,* Rev. A, Chapter 2 (P/N 903433, PE Corporation, Foster City, Calif.) January 1995). The optimal electrophoresis conditions, e.g., polymer, polymer concentration, pH, temperature, concentration of denaturing agent, employed in a particular separation depends on many factors, including the size range of the polynucleotides to be separated, their base compositions, whether they are single stranded or double stranded, and the nature of the classes for which information is sought by electrophoresis (Grossman, P. "High resolution DNA sequencing method using low viscosity medium", U.S. Pat. No. 5,374,527, issued Dec. 20, 1994). Accordingly application of the invention may require standard preliminary testing to optimize conditions for particular separations.

Polynucleotides labelled with the dyes of the present invention may also be labelled with moieties that affect the rate of electrophoretic migration, i.e. mobility-modifying labels. Mobility-modifying labels include polymers of ethyleneoxy units, —(CH$_2$CH$_2$O)$_n$— where n may be 1 to 100 (Grossman, etal "Method of DNA sequencing employing a mixed DNA-polymer chain probe", U.S. Pat. No. 5,624,800, Issued Apr. 29, 1997). Preferably, n is from 2 to 20. Specifically labelling fluorescein dye labelled polynucleotides with additional labels of polyethyleneoxy of discrete and known size allows for another dimension of separation by electrophoresis and detection, independent of the number of nucleotides in the polynucleotide. That is, polynucleotides of the same length may be discriminated upon the bases of spectrally resolvable dye labels and mobility-modifying labels. Polynucleotides bearing both dye labels and mobility-modifying labels may be formed enzymatically by ligation or polymerase extension of the single-labelled polynucleotide or nucleotide constituents. Alternatively, synthetic oligonucleotides may bear labels of dyes of the present invention and mobility-modifiers which are incorporated during automated synthesis, e.g. phosphoramidite reagents, or via post-synthesis coupling, e.g. NHS-label coupling to amino- or thiol-oligonucleotides.

Subsequent to electrophoretic separation, the dye-polynucleotide conjugates are detected by measuring the fluorescence emission from the dye labelled polynucleotides. To perform such detection, the labelled polynucleotides are illuminated by standard means, e.g. high intensity mercury vapor lamps, lasers, or the like. Preferably the illumination means is a laser having an illumination beam at a wavelength above about 450 nm. More preferably, the dye-polynucleotides are illuminated by laser light generated by an argon-ion or He-Ne gas laser or a solid-state diode laser. The fluorescence is then detected by a light-sensitive detector, e.g., a photomultiplier tube, a charged coupled device, or the like. Exemplary electrophoresis detection systems are described elsewhere (Hoff, etal "Real-time scanning fluorescence electrophoresis apparatus for the analysis of polynucleotide fragments", U.S. Pat. No. 5,543, 026, issued Aug. 6, 1996; Mathies, etal "Capillary array confocal fluorescence scanner and method", U.S. Pat. No. 5,274,240, issued Dec. 28, 1993; Hunkapiller, etal "Real time scanning electrophoresis apparatus for DNA sequencing", U.S. Pat. No. 4,811,218, issued Mar. 7, 1989).

EXAMPLES

The invention is further illustrated by the following examples, which are intended to be purely exemplary of the present invention and not to limit its scope in any way.

Example 1

Synthesis of 1,3-Dimethoxy-2-(Tol-2-yl)-Benzene 1

1,3-Dimethoxyphen-2-yl boronic acid:

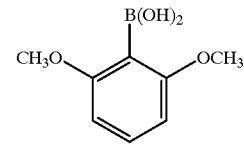

(10 g, 54.95 mmol, Frontier Scientific, Inc.), 2-bromotoluene (18.81 g, 110 mmol), glyme (200 ml), and tetrakis(triphenylphosphine) palladium, (Ph$_3$P)$_4$Pd° (4 g, 3.46 mmol) were stirred for 15 minutes followed by the addition of 8 g potassium carbonate in 35 ml of water (ref). After refluxing for 6 hr, the reaction mixture was poured into 800 ml of 1:1 mixture of water and ethyl acetate. The organic layer was washed with water (300 ml×2) and brine (200 ml×1), the solvent was removed, and the crude product was purified by silica-gel chromatography (hexane, ethyl acetate 0% to 10%) yielding 10.5 g (84%) of 1 (FIG. 1).

Example 2

Synthesis of 1,3-Dimethoxy-2-(Tol-2-yl)-4-Bromobenzene 2

1,3-Dimethoxy-2-(tol-2-yl)-benzene 1, (10 g, 43.86 mmol), N-bromosuccinimide (8.26 g, 46.4 mmol), and perchloric acid (70%, 0.5 ml) were mixed in dichloromethane (200 ml) and stirred for 4 hrs at room temperature. The reaction mixture was quenched with sodium bicarbonate solution (5%, 100 ml), the dichloromethane layer was washed with water (100 ml), brine (100 ml), and the solvent was removed. The crude product was purified by silica-gel chromatography eluting with hexane and ethyl acetate (0% to 10% ethyl acetate) yielding 10.8 g (80%) of 2.

Example 3

Synthesis of 1,3-Dimethoxy-2-(Tol-2-yl)-4-(Pyrid-3-yl)-Benzene 3

Pyridine-3-boronic acid (5.81 g, 47.27 mmol, Frontier Scientific, Inc.), 1,3-dimethoxy-2-(tol-2-yl)-4-bromobenzene (2) (10.7 g, 34.8mmol), glyme (200 mL), and tetrakis(triphenylphosphine) palladium (Ph$_3$P)$_4$Pd° (4 g, 3.46 mmol) were stirred for 15 minutes followed by the addition of potassium carbonate (16 g in 70 ml of water). After refluxing for 10 hr, the reaction mixture was poured into 800 ml of 1:1 mixture of water and ethyl acetate. The organic layer was washed with water (300 ml×2) and brine (200 ml), the solvent was removed, and the crude product was purified by silica-gel chromatography eluting with hexane and ethyl acetate (10% to 25% ethyl acetate) yielding 8.8 g (83%) of 3.

Example 4

Synthesis of 2-(Tol-2-yl)-4-(Pyrid-3-yl)-1,3-Dihydroxybenzene 4

1,3-Dimethoxy-2-(tol-2-yl)-4-(pyrid-3-yl)-benzene 3 (3.5 g, 11.46 mmol), acetic acid (30 ml), and hydrobromic acid (48%) (15 ml) were refluxed for 24 hr. After cooling the reaction mixture, most of the reagent was removed under reduced pressure; the residual acid was removed by mixing the concentrate with sodium bicarbonate solution (5%) (100 ml). The product was extracted into ethylacetate (100 ml), washed with water (100 ml×2) and brine (100 ml), and the ethyl acetate was evaporated. The crude product was purified by silica-gel chromatography eluting with dichloromethane and acetone (0% to 10% acetone) yielding 2.8 g (90%) of 4.

Example 5

Synthesis of Ketone 5

2-(Tol-2-yl)-4-(pyrid-3-yl)-1,3-dihydroxybenzene 4 (630 mg, 2.25 mmol), 2,5-dichlorotrimellitic anhydride:

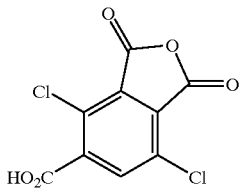

(Menchen, etal S. "4, 7-dichlorofluorescein dyes as molecular probes", U.S. Pat. No. 5,885,778, issued Mar. 23, 1999) (590 mg, 2.25 mmol), nitrobenzene (20 ml), and aluminum chloride in nitrobenzene (12 ml, 1M) were stirred at room temperature for 24 hrs. The reaction mixture was poured into a mixture of ice-water (50 ml), ethyl acetate (100 ml), and n-butanol (20 ml), followed by addition of 10% HCl (50 ml) to dissolve the aluminum salts. The organic layer was washed with water (50 ml×2) and brine (50 ml), and the solvent was evaporated to yield the product as a mixture of isomers 5a and 5b. Separation by silica-gel column chromatography with methanol in dichloromethane, (10% to 30% methanol), and (1%) acetic acid yielded 380 mg (31%) of the desired slow-moving isomer 5b, believed to have the structure shown in FIG. 1.

Example 6

1,3-Dimethoxynaphthalene 6

To 1,3-Dihydroxynaphthalene (15 g, 93.6 mmol) and potassium carbonate (20 g, 144.7 mmol) in acetone (200 ml) was added dimethyl sulfate (21 ml, 222 mmol). After stirring over-night the reaction mixture was mixed with 10% sodium hydroxide (100 ml) and extracted with ethyl acetate (200 ml×2) The organic layer was washed with water (100 ml×2), evaporated, and the residue stirred with ammonium hydroxide (50 ml) for 2 hrs to quench any unreacted dimethyl sulfate. Product was extracted with ethyl acetate (200 ml) and was washed with water (100 ml×2) and brine (100 ml). The solvent was evaporated yielding 15 g (85%) of 6.

Example 7

Bis-(1,3-Dimethoxynaphth-2-yl)-Dimethyltin 7

1,3-Dimethoxynaphthalene (6) (7.1 g, 37.73 mmol) was dissolved in anhydrous THF (60 ml), cooled to −70° C., and tetramethylethylenediamine (0.2 ml) was added followed by n-butyllithium (26 ml, 1.6 M in hexane). After stirring the solution cold for 30 minutes and at ambient temperature for 1 hr, the solution was cooled back to −20° C., and dimethyltin dichloride, $SnMe_2Cl_2$, (5.05 g in 20 ml THF) was added. The reaction mixture was stirred at ambient temperature for 2 hr, poured into water (100 ml) and extracted with ethyl acetate (100 ml). The organic layer was washed with water (50 ml), brine (50 ml), and evaporated. The residue was crystallized from hexane (50 ml), to yield 6.8 g (69 %) of 7.

Example 8

1,3-Dimethoxy-2-bromonaphthalene 8

Bis-(1,3-Dimethoxynaphth-2-yl)-dimethyltin 7 (11 g, 21 mmol) in THF (500 ml) was cooled to −30° C., and N-bromosuccinimide (8 g, 45 mmol) was added. After stirring at −30° C. for 2 hrs the reaction mixture was quenched with water (200 ml) and ethyl acetate (200 ml). The organic phase was washed with 10% hydrochloric acid (100 ml), water (100 ml×2), brine (100 ml), and evaporated. The crude product was purified by silica-gel chromatography, eluting with hexane-ethyl acetate (0% to 10% ethyl acetate), to yield 9 g (80%) of 8.

Example 9

2-(Pyrid-3-yl)-1,3-Dimethoxynaphthalene 9

Pyridine-3-boronic acid (3.94 g 32 mmol, Frontier Scientific, Inc.), 1,3-dimethoxy-2-bromonaphthalene 8 (6.6 g, 24.7 mmol), glyme (200 ml), and tetrakis (triphenylphosphine) palladium $(Ph_3P)_4Pd$ (3 g, 2.7 mmol) were stirred for 15 minutes followed by the addition of potassium carbonate (11.4 g in 50 mL of water). After refluxing over-night, the reaction mixture was poured into 800 ml of 1:1 water:ethyl acetate. The organic layer was washed with water (300 ml×2) and brine (200 ml), solvent was removed, and the crude product was purified by silica-gel chromatography eluting with dichloromethane and acetone (0% to 5% acetone) yielding 5.1 g (84%) of 9.

Example 10

2-(Tol-2-yl)-1,3-Dimethoxynaphthalene 10

This compound was prepared essentially by the same procedure as that in EXAMPLE 9 using 8 and tol-2-yl boronic acid (Frontier Scientific, Inc.).

Example 11

Synthesis of 2-(Pyrid-3-yl)-1,3-Dihydroxynaphthalene 11

This compound was prepared by the same procedure as used in EXAMPLE 4 using 2-(pyrid-3-yl)-1,3-dimethoxynaphthalene 9 to yield 11.

Example 12

Synthesis of 2-(Tol-2-yl)-1,3-Dihydoxynaphthalene 12

This compound was prepared by the same procedure as used in EXAMPLE 4 using 2-(tol-2-yl)-1,3-dimethoxynaphthalene 10 to yield 12.

Example 13

Synthesis of Dye 13

Ketone 5b (250 mg, 0.45 mmol) and 2-(pyrid-3-yl)-1,3-dihydroxynaphthalene 11 (109 mg, 0.45mmol) were mixed

Example 14

Synthesis of Dye 14

This dye was prepared by the same procedure as used in EXAMPLE 13 using 2-(tol-2-yl)-1,3-dihydoxynaphthalene 12 and 5.

Example 15

Synthesis of Dye 15

This dye was prepared by the same procedure as used in EXAMPLE 13 using 2-fluoro-1,3-dihydroxynaphthalene (Benson, etal "Asymmetric benzoxanthene dyes", U.S. Pat. No. 5,840,999, issued Nov. 24, 1998) and 5.

Example 16

Synthesis of Dye 16

2-(Tol-2-yl)-4-(pyrid-3-yl)-1,3-dihydroxybenzene 4 (52 mg, 0.28 mmol), 2,5-dichlorotrimellitic anhydride (Menchen, etal "4,7-dichlorofluorescein dyes as molecular probes", U.S. Pat. No. 5,885,778, issued Mar. 23, 1999), (36.5 mg, 14 mmol), and methanesulfonic acid, (1 ml), were heated and stirred at 130–135 ° C. for two hr. The solution was cooled to room temperature and then poured into ice-water (50 ml). The crude dye was extracted with n-butanol (50 ml×2) and the extract was washed with water (20 ml×2). Solvent was evaporated under vacuum to yield the crude dye as a mixture of two isomers. The isomers were separated by preparative thin layer chromatography, (silica gel; dichloromethane:methanol:acetic acid/100:10:2 (v:v:v) mobile phase) to yield 24 mg (30%) of the desired slower moving isomer of 16.

Example 17

Synthesis of 2,3-Dimethoxy-4-(Pyrid-3-yl)Benzene 17

2,4-Dimethoxyphenyl-4-yl boronic acid (0.9 g, 4.97 mmol, Frontier Scientific, Inc.), 3-bromopyridine (0.82 g, 5 mmol), tetrakis(triphenylphosphine) palladium $(Ph_3P)_4Pd°$ (0.65 g, 0.56 mmol), N,N-dimethylformamide (20 ml), and triethylamine (2.1 ml) were mixed and stirred at 110–120° C. for 16 hrs. The reaction mixture was poured into 100 ml of 1:1 mixture of water and ethylacetate, and the organic layer was washed with water (50 ml×2) and brine (50 ml). After removal of solvent the crude product was purified by silica-gel chromatography (0% to 10% acetone in dichloromethane) yielding 0.45 g (42.5%) of 17.

Example 18

Synthesis of 4-(Pyrid-3-yl)-1,3-Dihydroxybenzene 18

This compound was prepared by the same procedure as used in EXAMPLE 4 using 2,3-Dimethoxy-4-(Pyrid-3-yl) Benzene 17 to yield 18.

Example 19

Synthesis of Dye 19

This dye was prepared by the same procedure as used in EXAMPLE 16 using 4-(Pyrid-3-yl)-1,3-Dihydroxybenzene 18 and 2,5-dichlorotrimellitic anhydride.

Example 20

Synthesis of 2,3-Dimethoxy-4-(Pyrid-2-yl)Benzene 20

This compound was prepared by the same procedure as used in EXAMPLE 17 using 2,4-Dimethoxyphenyl-4-yl boronic acid and 2-bromopyridine to yield 20.

Example 21

Synthesis of 2,3-Dihydroxy-4-(Pyrid-2-yl)Benzene 21

This compound was prepared by the same procedure as used in EXAMPLE 4 using 2,3-dimethoxy-4-(pyrid-2-yl) benzene 20 to yield 21.

Example 22

Synthesis of Dye 22

This dye was prepared by the same procedure as used in EXAMPLE 16 using 4-(pyrid-3-yl)-1,3-dihydroxybenzene 21 and 2,5-dichlorotrimellitic anhydride.

Example 23

Synthesis of 1,3-Dimethoxy-4-(Quinon-3-yl) benzene 23

This compound was prepared using the same procedure as that used in EXAMPLE 17 using 1,3-dimethoxyphen-4-yl boronic acid and 3-bromoquinoline to yield 23.

Example 24

Synthesis of 1,3-Dihydroxy-4-(Quinon-3-yl)benzene 24

This compound was prepared by the same procedure as used in EXAMPLE 4 using 1,3-dimethoxy-4-(quinon-3-yl) benzene 23 to yield 24.

Example 25

Synthesis of Dye 25

This dye was prepared by the same procedure as used in EXAMPLE 16 using 1,3-dihydroxy-4-(quinon-3-yl) benzene 24 and 2,5-dichlorotrimellitic anhydride.

Example 26

Synthesis of 1,3-Dimethoxy-4-(Quinon-2-yl) benzene 26

This compound was prepared using the same procedure as that used in EXAMPLE 17 using 1,3-dimethoxyphen-4-yl boronic acid and 2-bromoquinoline to yield 26.

Example 27

Synthesis of 1,3-Dihydoxy-4-(Quinon-2-yl)benzene 27

This compound was prepared by the same procedure as used in EXAMPLE 4 using 1,3-dimethoxy-4-(quinon-2-yl) benzene 26 to yield 27.

Example 28

Synthesis of Dye 28

This dye was prepared by the same procedure as used in EXAMPLE 16 using 1,3-dihydoxy-4-(quinon-2-yl)benzene 27 and 2,5-dichlorotrimellitic anhydride.

Example 29

Synthesis of 1,3-Dimethoxy-2-(Pyrid-3-yl)benzene 29

This compound was prepared by the same procedure as used in EXAMPLE 1 using 1,3-dimethoxyphen-2-yl boronic acid and 3-bromopyridine to yield 29.

Example 30

Synthesis of 1,3-Dimethoxy-2-(Pyrid-3-yl)-4-bromobenzene 30

This compound was prepared by the same procedure as used in EXAMPLE 2 using 1,3-Dimethoxy-2-(Pyrid-3-yl)benzene 29 and N-bromosuccinimide to yield 30.

Example 31

Synthesis of 1,3-Dimethoxy-2-(Pyrid-3-yl)-4-phenylbenzene 31

This compound was prepared by the same procedure as used in EXAMPLE 3 using 1,3-dimethoxy-2-(pyrid-3-yl)-4-bromobenzene 30 and phenyl boronic acid to yield 31.

Example 32

Synthesis of 1,3-Dihydroxy-2-(Pyrid-3-yl)-4-phenylbenzene 32

This compound was prepared by the same procedure as used in EXAMPLE 4 using 1,3-dimethoxy-2-(pyrid-3-yl)-4-phenylbenzene 31 to yield 32.

Example 33

Synthesis of Dye 33

This dye was prepared by the same procedure as used in EXAMPLE 16 using 1,3-dihydoxy-2-(pyrid-3-yl)-4-phenylbenzene 32 and 2,5-dichlorotrimellitic anhydride.

Example 34

Synthesis of 1,3-Dimethoxy-2-(Tol-2-yl)-4-Phenylbenzene 34

This compound was prepared by the same procedure as used in EXAMPLE 3 using 1,3-dimethoxy-2-(tol-2-yl)-4-bromobenzene 2 and phenyl boronic acid to yield 34.

Example 35

Synthesis of 1,3-Dihydroxy-2-(Tol-2-yl)-4-Phenylbenzene 35

This compound was prepared by the same procedure as used in EXAMPLE 4 using 1,3-dimethoxy-2-(tol-2-yl)-4-phenylbenzene 34 to yield 35.

Example 36

Synthesis of Dye 36

This dye was prepared by the same procedure as used in EXAMPLE 16 using 1,3-dihydroxy-2-(tol-2-yl)-4-phenylbenzene 35 and 2,5-dichlorotrimellitic anhydride.

Example 37

Synthesis of 1,3-Dimethoxy-2-(Pyrid-2-yl)benzene 37

This compound was prepared by the same procedure as used in EXAMPLE 1 using 1,3-dimethoxyphen-2-yl boronic acid and 2-bromopyridine to yield 37.

Example 38

Synthesis of 1,3-Dimethoxy-2-(Pyrid-2-yl)-4-Bromobenzene 38

This compound was prepared by the same procedure as used in EXAMPLE 2 using 1,3-Dimethoxy-2-(Pyrid-2-yl)benzene 37 and N-bromosuccinimide to yield 38.

Example 39

Synthesis of 1,3-Dimethoxy-2-(Pyrid-2-yl)-4-(Naphth-2-yl)benzene 39

This compound was prepared by the same procedure as used in EXAMPLE 3 using 1,3-dimethoxy-2-(pyrid-2-yl)-4-bromobenzene 38 and naphth-2-yl boronic acid to yield 39.

Example 40

Synthesis of 1,3-Dihydroxy-2-(Pyrid-2-yl)-4-(Naphth-2-yl)benzene 40

This compound was prepared by the same procedure as used in EXAMPLE 4, demethylating 1,3-Dimethoxy-2-(Pyrid-2-yl)-4-(Naphth-2-yl)benzene 39 to yield 40.

Example 41

Synthesis of Dye 41

This dye was prepared by the same procedure as used in EXAMPLE 16 using 1,3-dihydroxy-2-(pyrid-2-yl)-4-(naphth-2-yl)benzene 40 and 2,5-dichlorotrimellitic anhydride.

Example 42

Properties of Dyes

Certain properties of some of the fluorescein dyes of the present invention were measured, Table 1.

TABLE 1

| Dye properties | | | |
|---|---|---|---|
| Dye Compound | Em. Max. (nm)[a] | FWHM[b] | Rel. Photostability[c] |
| 13 | 585 | 45 | 0.8 |
| 14 | 583 | 44 | |
| 15 | 591 | 45 | 0.25 |
| 16 | 570 | 36 | 0.78 |
| 19 | 554 | 37 | 1.5 |
| 22 | 556 | 37 | 2.2 |
| 25 | 562 | 38 | 1.6 |
| 28 | 564 | 39 | 1.5 |
| 33 | 571 | 38 | 1.0 |
| 36 | 572 | 38 | 1.2 |
| 41 | 575 | 39 | 1.1 |

[a] emission maxima of the acid form of the dye
[b] full width, half maximum
[c] relative to 5-carboxyfluorescein (5-FAM)

All publications and patent applications are herein incorporated by reference to the as if each individual publication

We claim:
1. A compound having the formula:

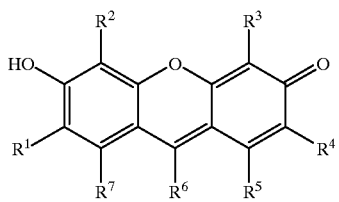

wherein:
at least one of $R^1$, $R^2$, $R^3$, $R^4$, $R^5$, or $R^7$ is an electron-deficient nitrogen heterocycle;

$R^1$, when taken alone, is H, F, Cl, ($C_1$–$C_6$) alkyl, ($C_1$–$C_6$) substituted alkyl, ($C_1$–$C_6$) alkoxy, sulfonate, sulfone, amino, imminium, amido, nitrile, reactive linking group, phenyl, substituted phenyl, aryl, substituted aryl, or heterocycle, or when taken together with $R^7$ is benzo or heterocycle;

$R^2$, when taken alone, is H, F, Cl, ($C_1$–$C_6$) alkyl, ($C_1$–$C_6$) substituted alkyl, ($C_1$–$C_6$) alkoxy, sulfonate, sulfone, amino, imminium, amido, nitrile, reactive linking group, phenyl, substituted phenyl, aryl, substituted aryl, or heterocycle;

$R^3$, when taken alone, is H, F, Cl, ($C_1$–$C_6$) alkyl, ($C_1$–$C_6$) substituted alkyl, ($C_1$–$C_6$) alkoxy, sulfonate, sulfone, amino, imminium, amido, nitrile, reactive linking group, phenyl, substituted phenyl, aryl, substituted aryl, or heterocycle;

$R^4$, when taken alone, is H, F, Cl, ($C_1$–$C_6$) alkyl, ($C_1$–$C_6$) substituted alkyl, ($C_1$–$C_6$) alkoxy, sulfonate, sulfone, amino, imminium, amido, nitrile, reactive linking group, phenyl, substituted phenyl, aryl, substituted aryl, or heterocycle, or when taken together with $R^5$ is benzo or heterocycle;

$R^5$, when taken alone, is H, F, Cl, ($C_1$–$C_6$) alkyl, ($C_1$–$C_6$) substituted alkyl, ($C_1$–$C_6$) alkoxy, sulfonate, sulfone, amino, imminium, amido, nitrile, reactive linking group, phenyl, substituted phenyl, aryl, substituted aryl, or heterocycle, or when taken together with $R^4$ is benzo or heterocycle;

$R^7$, when taken alone, is H, F, Cl, ($C_1$–$C_6$) alkyl, ($C_1$–$C_6$) substituted alkyl, (C–$C_6$) alkoxy, sulfonate, sulfone, amino, imminium, amido, nitrile, reactive linking group, phenyl, substituted phenyl, aryl, substituted aryl, or heterocycle, or when taken together with $R^1$ is benzo or heterocycle; and $R^6$ is selected from the group consisting of ($C_1$–$C_6$) alkyl, ($C_2$–$C_6$) alkene, ($C_2$–$C_6$) alkyne, cyano, heterocyclic aromatic, phenyl, and substituted phenyl having the structure:

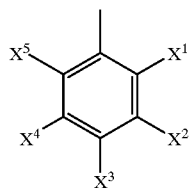

wherein $X^1$, $X^2$, $X^3$, $X^4$ and $X^5$ taken separately are H, Cl, F, ($C_1$–$C_6$) alkyl, ($C_2$–$C_6$) alkene, ($C_2$–$C_6$) alkyne, $CO_2H$, $SO_3H$, $CH_2OH$, or reactive linking group.

2. The fluorescein dye of claim 1 wherein the electron-deficient heterocycle is selected from the group consisting of 2-pyridyl, 3-pyridyl, 4-pyridyl, 2-quinolyl, 3-quinolyl, 4-quinolyl, 2-imidazole, 4-imidazole, 3-pyrazole, 4-pyrazole, pyridazine, pyrimidine, pyrazine, cinnoline, pthalazine, quinazoline, quinoxaline, 3-(1,2,4-N)-triazolyl, 5-(1,2,4-N)-triazolyl, 5-tetrazolyl, 4-(1-O, 3-N)-oxazole, 5-(1-O, 3-N)-oxazole, 4-(1-S, 3-N)-thiazole, 5-(1-S, 3-N)-thiazole, 2-benzoxazole, 2-benzothiazole, 4-(1,2,3-N)-benzotriazole, and benzimidazole.

3. The fluorescein dye of claim 1 wherein $R^4$ taken together with $R^5$ is benzo.

4. The fluorescein dye of claim 1 wherein $R^1$ taken together with $R^7$ is benzo.

5. The fluorescein dye of claim 1 in which $R^6$ is a substituted phenyl having the structure:

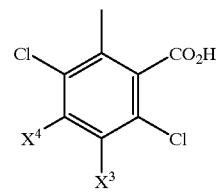

6. The fluorescein dye of claim 5 wherein one of $X^3$ and $X^4$ is carboxyl and the other is hydrogen.

7. The fluorescein dye of claim 1 wherein $R^1$, $R^2$, $R^3$ and $R^4$ each taken separately are phenyl or substituted phenyl.

8. The fluorescein dye of claim 1 wherein $R^1$, $R^2$, $R^3$ and $R^4$ each taken separately are naphthyl or substituted naphthyl.

9. The fluorescein dye of claim 1 wherein $R^2$ and $R^3$ each taken separately are fluoro or chloro.

10. The fluorescein dye of claim 1 wherein $R^2$ and $R^3$ each taken separately are 2-pyridyl or 3-pyridyl.

11. The fluorescein dye of claim 1 wherein $R^2$ and $R^3$ each taken separately are 2-quinolyl or 3-quinolyl.

12. The fluorescein dye of claim 1 wherein $R^5$ and $R^7$ are hydrogen.

13. The fluorescein dye of claim 1 in which the reactive linking group is selected from the group consisting of succinimidyl ester, isothiocyanate, sulfonyl chloride, 2,6-dichlorotriazinyl, pentafluorophenyl ester, phosphoramidite, maleimide, haloacetyl, and iodoacetamide.

14. Fluorescein dyes having the structures:
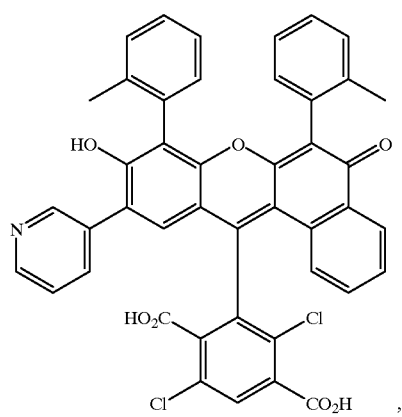
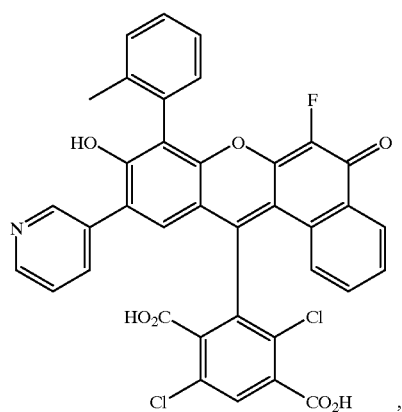
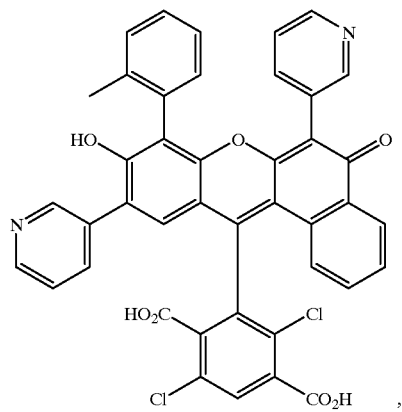
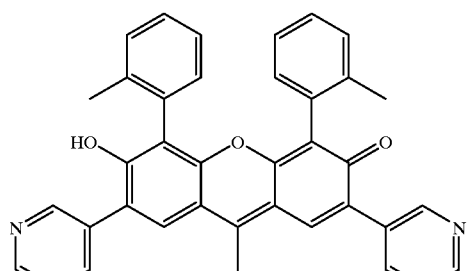
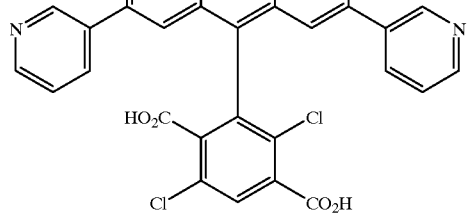
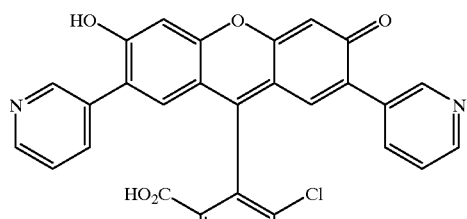
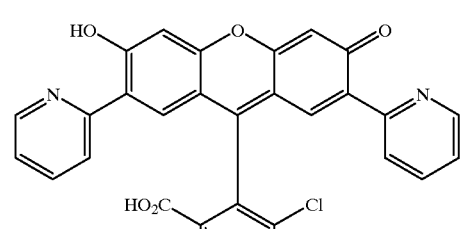
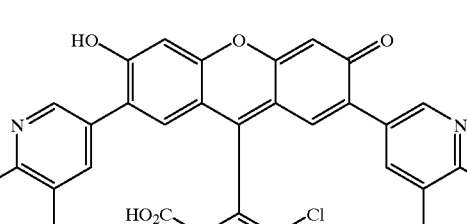

-continued

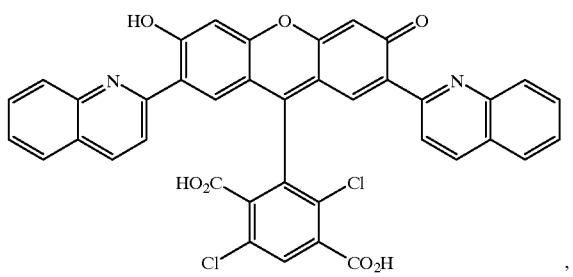

,

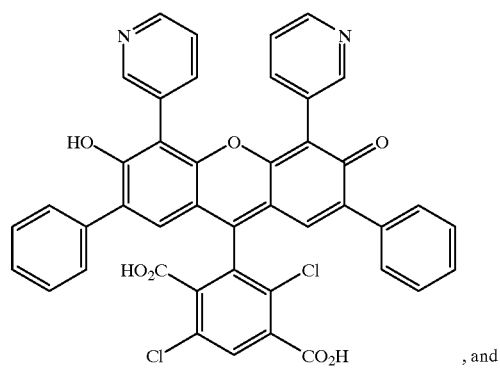

, and

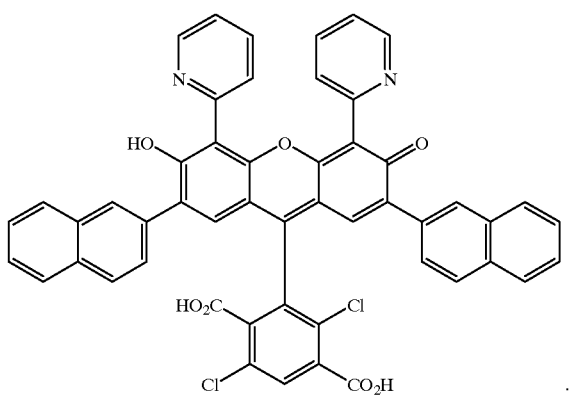

15. A method of labelling a substrate with a fluorescein dye of claim 1, comprising the step of reacting the substrate with the reactive linking group of the fluorescein dye wherein a substrate-dye conjugate is formed.

16. The method of claim 15 wherein the reactive linking group is N-hydroxysuccinimide.

17. The method of claim 15 wherein the reactive linking group is phosphoramidite.

18. The method of claim 15 wherein the substrate is selected from the group consisting of a polynucleotide, a nucleotide, a nucleoside, a peptide, a protein, a carbohydrate, a ligand, a particle, and a surface.

19. The method of claim 18 wherein the particle is a nanoparticle, a microsphere, a bead, and a liposome.

20. The method of claim 18 wherein the surface is glass.

21. An energy transfer dye compound comprising:
a donor dye capable of absorbing light at a first wavelength and emitting excitation energy in response linked by a linker to an acceptor dye capable of absorbing the excitation energy emitted by the donor dye and fluorescing at a second wavelength in response;
wherein at least one of the donor dye and acceptor dye is a fluorescein dye of claim 1.

22. The energy transfer dye of claim 21 wherein the linker has the structure:

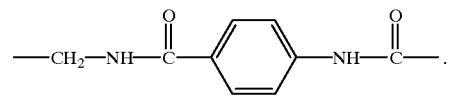

23. The energy transfer dye of claim 21 wherein the linker has the structure:

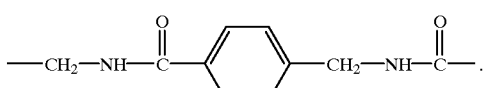

24. The energy transfer dye of claim 21 in which the linker has the structure:

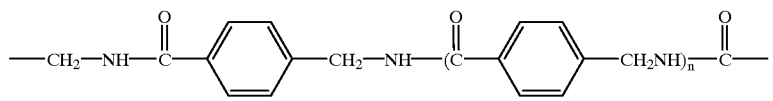

wherein n is 1 or 2.

25. A labelled nucleoside or nucleotide having the formula:

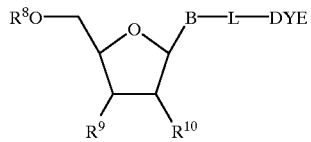

wherein DYE is a fluorescein dye of claim 1 or an energy transfer dye of claim 23;

B is a nucleobase;

$R^8$ is H, monophosphate, diphosphate, triphosphate, thiophosphate, or phosphate analog;

$R^9$ and $R^{10}$, when taken alone, are each independently H, HO, F, and a moiety which blocks polymerase-mediated target-directed polymerization, or when taken together form 2'-3'-didehydroribose; and L is a linker.

26. The labelled nucleoside or nucleotide of claim 25 wherein B is selected from the group consisting of uracil, thymine, cytosine, adenine, 7-deazaadenine, guanine, and 8-deazaguanosine.

27. The labelled nucleoside or nucleotide of claim 25 in which L is:

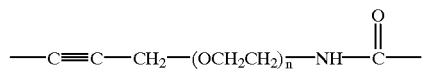

wherein n is 0, 1, or 2.

28. The labelled nucleoside or nucleotide of claim 25 which is enzymatically incorporatable.

29. The labelled nucleoside or nucleotide of claim 25 which is a terminator.

30. The terminator nucleotide of claim 29 which has the structure:

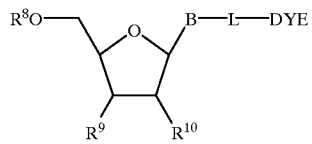

wherein DYE is a fluorescein dye;

B is a nucleobase;

$R^8$ is triphosphate, α-thiotriphosphate, or triphosphate analog;

$R^9$ and $R^{10}$, when taken alone, are each independently H, F, and a moiety which blocks polymerase-mediated target-directed polymerization, or when taken together form 2'-3'-didehydroribose; and L is a linker.

31. The labelled nucleoside or nucleotide of claim 25 which is enzymatically extendable.

32. A labelled oligonucleotide having the formula:

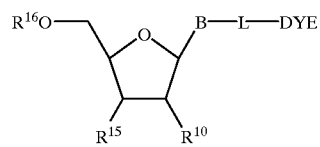

wherein the oligonucleotide comprises 2 to 100 nucleotides;

DYE is a fluorescein dye of claim 1 or an energy transfer dye of claim 21;

B is a nucleobase;

L is a linker;

$R^{10}$ is H, OH, halide, azide, amine, alkylamine, alkyl ($C_1$–$C_6$), allyl, alkoxy ($C_1$–$C_6$), $OCH_3$, or $OCH_2CH=CH_2$;

$R^{15}$ is H, phosphate, internucleotide phosphodiester, or internucleotide analog; and $R^{16}$ is H, phosphate, internucleotide phosphodiester, or internucleotide analog.

33. A labelled oligonucleotide having the formula:

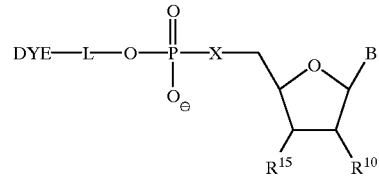

wherein the oligonucleotide comprises 2 to 100 nucleotides;

DYE is a fluorescein dye of claim 1;

X is O, NH, or S;

B is a nucleobase;

L is a linker;

$R^{10}$ is H, OH, halide, azide, amine, alkylamine, alkyl ($C_1$–$C_6$), allyl, alkoxy ($C_1$–$C_6$), $OCH_3$, or $OCH_2CH=CH_2$; and $R^{15}$ is internucleotide phosphodiester or internucleotide analog.

34. The labelled oligonucleotide of claim 33 in which L is alkyldiyl ($C_1$–$C_{12}$).

35. The labelled oligonucleotide of claim 33 in which L is a mobility-modifier comprising —$(CH_2CH_2O)_n$—, where n is 1 to 100.

36. A phosphoramidite compound having the formula:

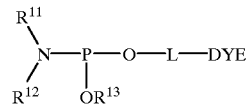

wherein DYE is a fluorescein dye of claim 1 or an energy transfer dye of claim 21;

L is a linker;

$R^{11}$ and $R^{12}$ taken separately are selected from the group consisting of alkyl ($C_1$–$C_{12}$), alkene, aryl, and cycloalkyl containing up to 10 carbon atoms; or $R^{11}$ and $R^{12}$ taken together with the nitrogen atom form a saturated nitrogen heterocycle; and $R^{13}$ is a phosphite ester protecting group.

37. The phosphoramidite compound of claim 36 wherein $R^{13}$ is selected from the group consisting of methyl, 2-cyanoethyl, and 2-(4-nitrophenyl)ethyl.

38. The phosphoramidite compound of claim 36 wherein $R^{11}$ and $R^{12}$ are each isopropyl.

39. The phosphoramidite compound of claim 36 wherein $R^{11}$ and $R^{12}$ taken together is morpholino.

40. The phosphoramidite compound of claim 36 wherein L is alkyldiyl ($C_1$–$C_{12}$).

41. The phosphoramidite compound of claim 36 wherein the fluorescein dye is attached at $R^6$ by a linker.

42. The phosphoramidite compound of the structure:

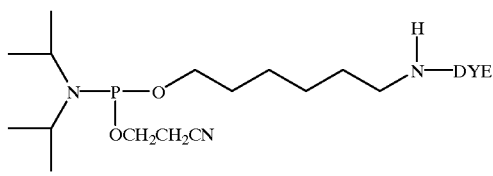

wherein DYE is a fluorescein dye of claim 1.

43. A phosphoramidite compound having the formula

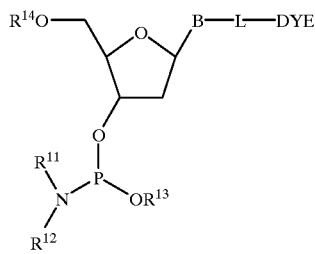

wherein DYE is a fluorescein dye of claim 1 or an energy transfer dye of claim 21;

B is a nucleobase;

L is a linker;

$R^{11}$ and $R^{12}$ taken separately are selected from the group consisting of alkyl ($C_1$–$C_6$), alkene, aryl, and cycloalkyl containing up to 10 carbon atoms; or $R^{11}$ and $R^{12}$ taken together with the nitrogen atom form a saturated nitrogen heterocycle;

$R^{13}$ is a phosphite ester protecting group; and $R^{14}$ is an acid-cleavable hydroxyl protecting group.

44. The phosphoramidite compound of claim 43 wherein $R^{13}$ is selected from the group consisting of methyl, 2-cyanoethyl, and 2-(4-nitrophenyl)ethyl.

45. The phosphoramidite compound of claim 43 wherein $R^{11}$ and $R^{12}$ are each isopropyl.

46. The phosphoramidite compound of claim 43 wherein $R^{11}$ and $R^{12}$ taken together is morpholino.

47. The compound of claim 43 wherein L is:

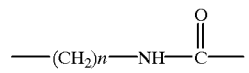

and n ranges from 2 to 10.

48. The compound of claim 43 wherein L is:

and n is 0, 1, or 2.

49. The compound of claim 43 wherein L is

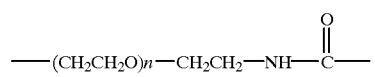

and n ranges from 1 to 10.

50. The compound of claim 43 wherein B is selected from the group consisting of uracil, thymine, cytosine, adenine, 7-deazaadenine, guanine, and 8-deazaguanosine.

51. A method of synthesizing a labelled oligonucleotide comprising the step of coupling a phosphoramidite compound of claim 36 to an oligonucleotide on a solid support.

52. A method of synthesizing a labelled oligonucleotide comprising the step of coupling a nucleoside phosphoramidite reagent to a solid support wherein the solid support is labelled with a dye according to claim 1 or an energy transfer compound of claim 21.

53. A method of generating a labelled primer extension product, comprising the step of enzymatically extending a primer-target hybrid in the presence of a mixture of enzymatically-extendable nucleotides capable of supporting continuous primer extension and a terminator, wherein said primer or said terminator is labelled with a dye according to claim 1 or an energy transfer compound of claim 21.

54. A method of oligonucleotide ligation, comprising the steps of:
 annealing two probes to a target sequence and
 forming a phosphodiester bond between the 5' terminus of one probe and the 3' terminus of the other probe;
 wherein one or both probes are labelled with a dye according to claim 1 or an energy transfer compound of claim 21.

55. A method of fragment analysis comprising the steps of:
 subjecting polynucleotide fragments, the fragments being labelled with a fluorescein dye of claim 1 or an energy transfer compound of claim 21, to a size-dependent separation process; and
 detecting the labelled polynucleotide fragment subsequent to the separation process.

56. The method of claim 55 wherein the fragments are labelled with a mobility-modifying label.

57. The method of claim 55 wherein the fragments are formed by ligation.

58. The method of claim 55 wherein the size-dependent separation process is electrophoresis and the labelled polynucleotide fragment is detected by fluorescence.

59. A method of amplification comprising the steps of:
 annealing two or more primers to a target DNA sequence and
 extending the primers by polymerase and a mixture of enzymatically-extendable nucleotides;
 wherein a primer or a nucleotide is labelled with a dye according to claim 1.

60. A method of amplification comprising the steps of:
 annealing two or more primers and a fluorescent dye-quencher probe to a target DNA sequence and extending the primers by polymerase and a mixture of enzymatically-extendable nucleotides;

wherein the probe is labelled with a dye according to claim 1.

61. A kit for labelling an oligonucleotide, comprising a dye including a reactive linking group according to claim 1 and an oligonucleotide.

62. A kit for labelling an oligonucleotide, comprising a phosphoramidite compound according to claim 36 and an oligonucleotide.

63. A kit for generating a labelled primer extension product, comprising enzymatically-extendable nucleotides capable of supporting continuous primer extension, a terminator and a primer, wherein said primer or said terminator is labelled with a dye according to claim 1.

64. A kit for generating a labelled primer extension product, comprising enzymatically-extendable nucleotides capable of supporting continuous primer extension, a terminator and a primer, wherein said primer or said terminator is labelled with an energy transfer dye of claim 21.

65. A kit for generating a labelled primer extension product, comprising enzymatically-extendable nucleotides capable of supporting continuous primer extension, a terminator and a primer, wherein said primer or said terminator is labelled with a dye according to claim 14.

66. The kit of claim 65 in which the terminator is a set of four different terminators, one which terminates at a target A, one which terminates at a target G, one which terminates at a target C and one which terminates at a target T or U.

67. The kit of claim 66 in which the set of four different terminators is a set of mobility-matched terminators.

* * * * *